United States Patent
Cho et al.

(10) Patent No.: US 10,798,986 B2
(45) Date of Patent: Oct. 13, 2020

(54) SHOE

(71) Applicant: SALTED VENTURE CO., LTD., Seoul (KR)

(72) Inventors: Hyung Jin Cho, Seoul (KR); Kyung Hoon Kang, Seoul (KR)

(73) Assignee: SALTED VENTURE CO., LTD., Seoul (KR)

( * ) Notice: Subject to any disclaimer, the term of this patent is extended or adjusted under 35 U.S.C. 154(b) by 83 days.

(21) Appl. No.: 16/078,529

(22) PCT Filed: Nov. 28, 2016

(86) PCT No.: PCT/KR2016/013796
§ 371 (c)(1),
(2) Date: Aug. 21, 2018

(87) PCT Pub. No.: WO2017/146350
PCT Pub. Date: Aug. 31, 2017

(65) Prior Publication Data
US 2020/0154817 A1  May 21, 2020

(30) Foreign Application Priority Data

Feb. 22, 2016 (KR) .................. 10-2016-0020363
Nov. 28, 2016 (KR) .................. 10-2016-0159091

(51) Int. Cl.
*A43B 3/00* (2006.01)
*A43B 13/14* (2006.01)

(52) U.S. Cl.
CPC ............ *A43B 3/0005* (2013.01); *A43B 13/14* (2013.01)

(58) Field of Classification Search
CPC .............................. A43B 3/0005; A43B 13/14
(Continued)

(56) References Cited

U.S. PATENT DOCUMENTS 5,373,651 A * 12/1994 Wood ..................... A43B 3/00
36/1
5,500,635 A *  3/1996 Mott ................... A43B 1/0072
310/311

(Continued)

FOREIGN PATENT DOCUMENTS

KR   10-2009-0049572    5/2009
KR      20140004206     1/2014
(Continued)

OTHER PUBLICATIONS

International Seach Report issued in International Patent Application No. PCT/KR2016/013796 dated May 12, 2017 and English translation of same.

(Continued)

*Primary Examiner* — Marie D Bays
(74) *Attorney, Agent, or Firm* — Studebaker & Brackett PC

(57) ABSTRACT

The present invention provides a shoe capable of maximizing sensing sensitivity. The shoe comprises: an outsole including a forefoot area, a midfoot area, and a rear foot area; an upper structure coupled to the outsole; and a sensing system embedded in the outsole, wherein the sensing system includes a first sensor corresponding to the forefoot area or the midfoot area and a second sensor corresponding to the rear foot area, and the second sensor is embedded deeper than the first sensor into the outsole from the top surface thereof.

11 Claims, 20 Drawing Sheets

(58) Field of Classification Search
USPC .................................................. 36/136, 114
See application file for complete search history.

(56) References Cited

U.S. PATENT DOCUMENTS

| | | | | |
|---|---|---|---|---|
| 6,160,254 A * | 12/2000 | Zimmerman | ........ | A43B 3/0005 250/225 |
| 2010/0063778 A1* | 3/2010 | Schrock | ................. | A61B 5/486 702/188 |
| 2010/0199524 A1* | 8/2010 | Grun | ......................... | G01L 1/14 36/103 |
| 2013/0190903 A1* | 7/2013 | Balakrishnan | ....... | A61B 5/0077 700/91 |
| 2013/0213147 A1* | 8/2013 | Rice | ....................... | A43B 7/088 73/862.046 |
| 2015/0177081 A1* | 6/2015 | Steier | .................. | A61B 5/6807 600/592 |
| 2016/0174899 A1* | 6/2016 | Besnard | ............... | A43B 3/0005 600/595 |
| 2016/0252412 A1* | 9/2016 | McMillen | ................. | G01L 1/18 73/774 |
| 2016/0345891 A1* | 12/2016 | Kirby | ................... | A43B 13/181 |
| 2017/0115171 A1* | 4/2017 | Huang | ................. | A61B 5/1038 |
| 2018/0070877 A1* | 3/2018 | Tian | ..................... | A43B 3/0005 |
| 2018/0169474 A1* | 6/2018 | Reddy | ................ | A63B 24/0062 |
| 2020/0046061 A1* | 2/2020 | Mazzoleni | ........... | A61B 5/6807 |

FOREIGN PATENT DOCUMENTS

| KR | 20150041903 | 4/2015 |
|---|---|---|
| KR | 20150080688 | 7/2015 |
| KR | 101547653 | 8/2015 |
| KR | 101757377 | 7/2017 |

OTHER PUBLICATIONS

Written Opinion issued in International Patent Application No. PCT/KR2016/013796 dated May 12, 2017.
Notice of Allowance issued in related Korean Patent Application No. 10-2016-0159091 dated Nov. 20, 2018.

* cited by examiner

SHOE

CROSS REFERENCE TO RELATED APPLICATIONS

The present application is a National Stage of International Application No. PCT/KR2016/013796, filed on Nov. 28, 2016, which claims priority to Korean Patent Application No. 10-2016-0020363, filed on Feb. 22, 2016, and Korean Patent Application No. 10-2016-0159091, filed on Nov. 28, 2016, the entire contents of each of which are being incorporated herein by reference.

BACKGROUND

Technical Field

The present invention relates to a shoe, and more particularly, to providing a shoe including an outsole in which a sensing system is installed.

Background Art

Feet are appendages which support a whole weight of a human body and are significant appendages which perform a cushioning function of relieving a variety of shocks. Each human foot has 52 bones corresponding to about ¼ of all bones thereof, 64 muscles, 76 joints, and 214 ligaments which are intricately entwined so that a human being can walk upright or do exercise. Also, soles of a human being are very important sensory organs in which a variety of nerves related to functions of many internal organs of a human body are gathered.

Meanwhile, shoes are a generic term for items put on feet and may be used for protecting feet and as decoration. In daily life and while walking, running, playing a variety of games such as golf, baseball, and the like, shoes are worn.

SUMMARY

Technical Problem

The present invention is directed to providing a shoe capable of maximizing sensing sensitivity.

The present invention is also directed to providing an apparatus capable of generating a calculation value based on a plurality of sensing values provided from the shoe and matching and displaying a motion image of a user with the calculation value with a time.

It should be noted that objects of the present invention are not limited to the above-described objects, and other objects of the present invention will be apparent to those skilled in the art from the following descriptions.

Technical Solution

One aspect of the present invention provides a shoe including an outsole which includes a forefoot area, a mid-foot area, and a rear foot area, an upper structure combined with the outsole, and a sensing system embedded in the outsole. Here, the sensing system includes a first sensor corresponding to the forefoot area or the mid-foot area and a second sensor corresponding to the rear foot area, and the second sensor is embedded deeper from a top surface of the outsole than the first sensor.

The shoe may further include a third sensor which is spaced further apart from a front end of the outsole than the first sensor and is disposed closer to the front end of the outsole than the second sensor. Here, the third sensor may be embedded shallower with respect to the top surface of the outsole than the second sensor.

The third sensor may be embedded deeper with respect to the top surface of the outsole than the first sensor.

The first sensor to the third sensor may be embedded at depths from 10% to 70% from the top surface of the outsole.

The first sensor to the third sensor may be embedded at depths from 10% to 40% from the top surface of the outsole.

The first sensor may be embedded at a depth 10% to 20% from the top surface of the outsole. The third sensor may be embedded at a depth 20% to 30% from the top surface of the outsole. The second sensor may be embedded at a depth 30% to 40% from the top surface of the outsole.

The shoe may include a first weight section and a second weight section heavier than the first weight section. A sensing value of the first sensor according to weight may have a linear shape in the first weight section and a nonlinear shape in the second weight section. A sensing value of the second sensor according to weight may have a nonlinear shape in the first weight section and a linear shape in the second weight section.

The sensing system may include a control module including a top surface and a rear surface. The sensing system may include a first flexible circuit board connected to the top surface of the control module and a second flexible circuit board connected to the rear surface of the control module. The first sensor may be disposed on the first flexible circuit board. The second sensor may be disposed on the second flexible circuit board.

The sensing system may further include a control module which receives sensing signals from the first sensor and the second sensor and communicates with an external device through an antenna. The control module may be disposed corresponding to an inside of an arch area, and the antenna may be disposed closer to the outside of the shoe than the control module.

The first sensor and the second sensor may be film-type pressure sensors.

Another aspect of the present invention provides a shoe including an outsole, an upper structure combined with the outsole and a sensing system embedded in the outsole. Here, the sensing system includes a first sensor and a second sensor. The first sensor is disposed closer to a front end of the outsole than the second sensor, and a disposition depth of the first sensor is shallower than a disposition depth of the second sensor.

Still another aspect of the present invention provides a shoe including an outsole which includes a forefoot area, a mid-foot area, and a rear foot area, an upper structure combined with the outsole, and a sensing system embedded in the outsole. Here, the sensing system includes a first sensor corresponding to the forefoot area or the mid-foot area and a second sensor corresponding to the rear foot area. The shoe includes a first weight section and a second weight section heavier than the first weight section. A sensing value of the first sensor according to weight has a linear shape in the first weight section and a nonlinear shape in the second weight section. A sensing value of the second sensor according to weight has a nonlinear shape in the first weight section and a linear shape in the second weight section.

Yet another aspect of the present invention provides an apparatus including a transmission and reception module which receives a plurality of sensing values from a shoe in which a plurality of sensors are embedded in an outsole thereof, a processor which generates at least one calculation value on the basis of the plurality of sensing values and matches a motion image of a user with the calculation value according to a time, and a display module which shows the motion image of the user and the calculation value, which are matched, at the same time.

The calculation value may include a user's center of gravity.

The calculation value may further include a ratio between a sum of sensing values sensed at fronts of a left shoe and a right shoe and a sum of sensing values sensed at backs of the left shoe and the right shoe.

The calculation value may further include a ratio between a sum of sensing values sensed at a right shoe and a sum of sensing values sensed at a left shoe.

The display module may display a first screen to a third screen which are separated from one another. A motion image of the user may be displayed in the first screen. The user's center of gravity may be displayed in the second screen. A ratio between a sum of sensing values sensed at a right shoe and a sum of sensing values sensed at a left shoe may be displayed in the third screen.

A screen may be converted according to an instruction of the user such that a ratio between a sum of sensing values sensed at fronts of a left shoe and a right shoe and a sum of sensing values sensed at backs of the left shoe and the right shoe is displayed in the third screen.

The display module may display a first screen to a fourth screen which are separated from one another. A motion image of the user may be displayed in the first screen. A motion image of another user may be displayed in the second screen. A calculation value of the user may be displayed in the third screen. A calculation value of the other user may be displayed in the fourth screen.

The motion image of the user and the motion image of the other user may overlap with each other or the calculation value of the user and the calculation value of the other user may overlap with each other according to a user's instruction to be displayed as such.

Details of other embodiments are included in a detailed description and drawings.

MODES OF THE INVENTION

Figure 1:
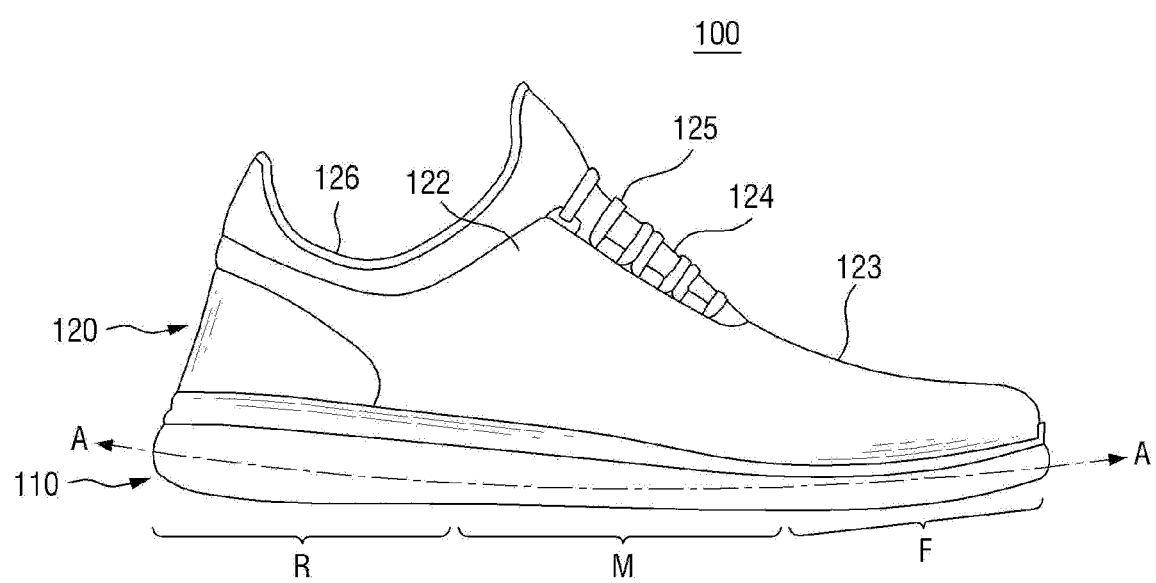
FIG. 1 is a side view illustrating a shoe according to some embodiments of the present invention.

Hereinafter, exemplary embodiments of the present invention will be described in detail with reference to the attached drawings. Advantages and features of the present invention and methods of achieving them will be specified with reference to the attached drawings and following detailed-described embodiments. However, the present invention is not limited to the embodiments described below and may be embodied in various different forms. The embodiments are provided merely to completely disclose the present invention and completely inform one of ordinary skill in the art of the scope of the present invention. The present invention is defined by only the scope of the claims. Throughout the specification, like reference numerals refer to like elements.

When it is stated that an element or a layer is "on" another element or layer, not only being directly on another element or layer but also interposing another layer or element therebetween are included. On the other hand, when it is stated that an element is "directly on" another, there is no other element or layer interposed therebetween.

Terms which are spatially relative such as "below," "beneath," "lower," "above," "upper," and the like may be used to easily describe a relationship between one element or component and another element or component as shown in the drawings. The spatially relative terms should be understood as terms which include different directions of an element when the element is used or operates, in addition to directions shown in the drawings. For example, when an element shown in the drawing is turned upside down, the element described as being "below" or "beneath" another element may be disposed "above" the other element. Accordingly, "below" which is an exemplary term may include both downward and upward directions. The element may be arranged in another direction such that the spatially relative terms may be understood according to arrangement.

Although first, second, and the like are used for describing a variety of elements, components, and/or sections, the elements, components, and/or sections are not limited to the terms. These terms are used for merely distinguishing one element, component, or section from another element, component, or section. Accordingly, a first element, a first component, or a first section which is stated below may be a second element, a second component, or a second section within the technical concept of the present invention.

The terms used herein are for explaining embodiments but are not intended to limit the present invention. Throughout the specification, unless particularly defined otherwise, singular forms include plural forms. The terms "comprises" and/or "comprising" are used herein as meanings which do not exclude presence or addition of one or more other components, stages, operations, and/or elements in addition to stated components, stages, operations, and/or elements.

Unless defined otherwise, all the terms (including technical and scientific terms) have the same meaning as commonly understood by one of ordinary skill in the art. Also, terms such as those defined in commonly used dictionaries should not be interpreted in an idealized or excessively formal sense unless defined otherwise.

Hereinafter, embodiments of the present invention will be described in detail with reference to the attached drawings. In the description with reference to the attached drawings, irrelative to reference numerals, like or corresponding components will be referred to as the same reference numerals and an overlapping description thereof will be omitted.

Figure 2:
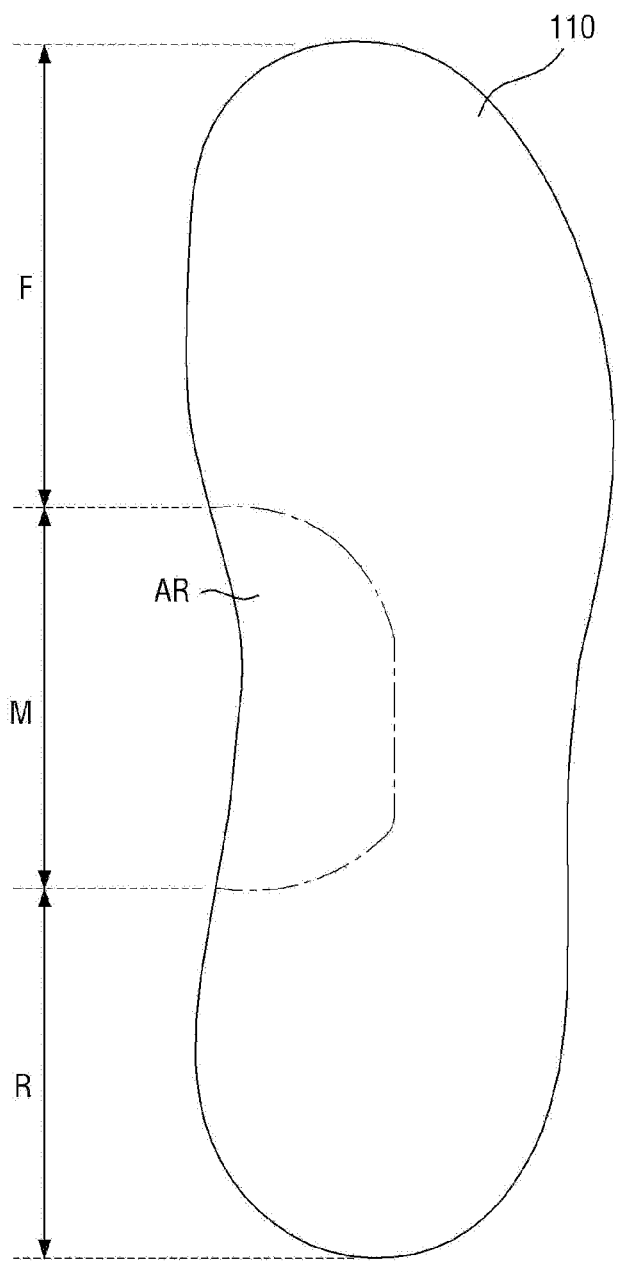
FIG. 2 is a top view illustrating an outsole of FIG. 1.

FIG. 1 is a side view illustrating a shoe according to some embodiments of the present invention. FIG. 2 is a top view illustrating an outsole of FIG. 1.

Although a training shoe is illustrated as an example in FIG. 1, the shoe is not limited thereto. The present invention may be applied to a variety of shapes of training shoes, for example, running shoes, walking shoes, tennis shoes, baseball shoes, basketball shoes, soccer shoes, and the like and may be applied to a variety of shapes of shoes such as loafers, sneakers, straight tip shoes, wing tip shoes, monk strap shoes, and the like.

Referring to FIGS. 1 and 2, a shoe 100 includes an outsole 110, an insole, an upper structure 120, and the like.

The outsole 110 is located at a bottom of the shoe 100 and refers to a part which comes into contact with the ground. The outsole 110 may be manufactured using a material such as leather, rubber, silicone, and the like but the present invention is not limited thereto.

Also, the outsole 110 may include, for example, a forefoot area F, a rear foot area R, and a mid-foot area M disposed between the forefoot area F and the rear foot area R. A ratio between the forefoot area F, the mid-foot area M, and the rear foot area R may be, for example, F:M:R=40:30:30.

Meanwhile, an arch area AR is a part corresponding to an arch area of a foot. The arch area AR may be a part of the mid-foot area M and may be disposed, for example, on an inside of the mid-foot area M (that is, a side on which another foot is present.

The upper structure 120 is connected and/or fixed to the outsole 110 to define a space for inserting a foot therein. The upper structure 120 may be formed of, for example, one or more of leather, artificial leather, natural or synthetic fabric, a polymer foaming material, mesh fabric, felt, a non-quilted polymer, and a rubber material but the present invention is not limited thereto.

The upper structure 120 includes a side surface area 122, a shoe top area 123, and the like.

The side surface area 122 is disposed to extend along a side surface of a foot.

The shoe top area 123 is formed corresponding to a top surface of a foot or a foot top area. Also, a space 124 having a lace 125 is formed on the shoe top area 123 such that the entire size of the shoe 100 may be adjusted using the lace. That is, a closing mechanism for allowing the shoe 100 to be well worn on a foot is applied.

Also, a foot is inserted in the shoe 100 through an opening 126.

Meanwhile, an insole is disposed on the outsole 110. The insole is a surface with which a foot comes into direct contact.

Meanwhile, an embedded sensing system 105 (refer to FIG. 4) is installed in the outsole 110 according to some embodiments of the present invention. The sensing system 105 may sense a pressure generated by a foot by using a plurality of sensors 201a, 202a, 203a, and 204a (refer to FIGS. 3 and 4) and may communicate with an external device through an antenna. Since the sensing system 105 is completely embedded in the outsole 110, the outsole 110 is detachable from the upper structure 120 for a manufacturing process and after-sales maintenance. A detachment method may be changed according to a combination method (mechanical combination, chemical combination, and the like) of the outsole 110 and the upper structure 120.

The sensing system 105 will be described in detail with reference to FIGS. 3 to 15.

Figure 3:
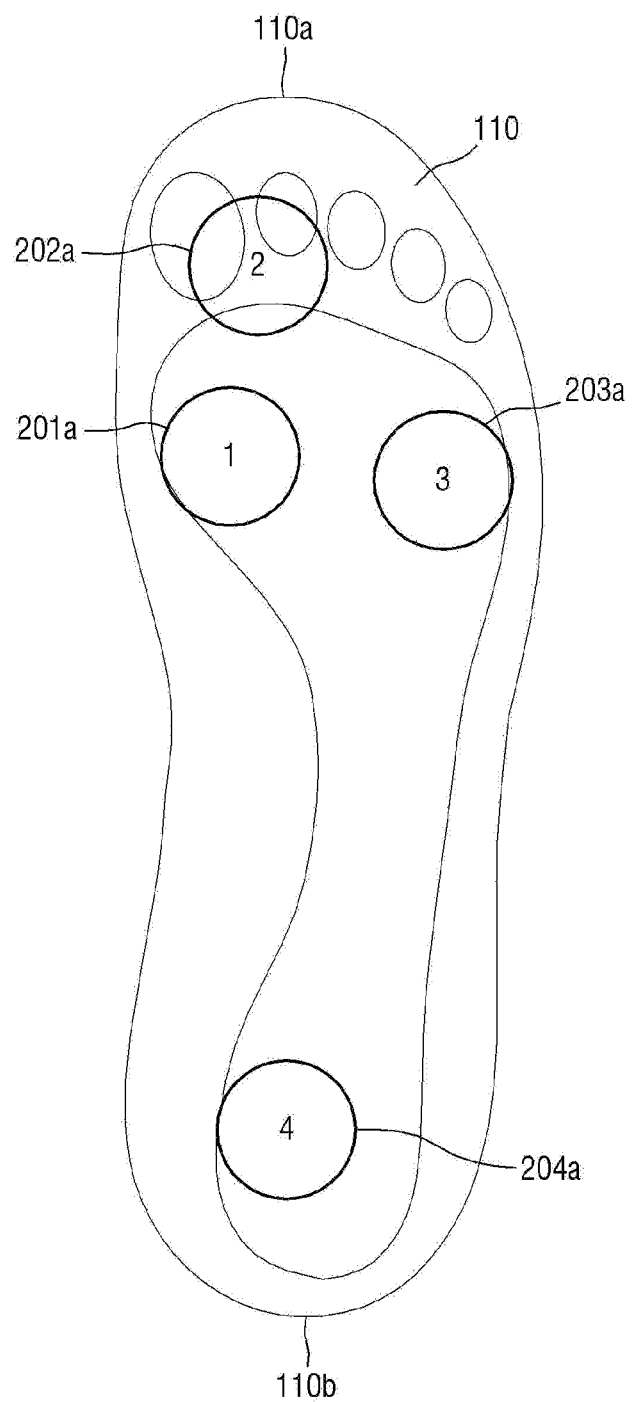
FIGS. 3 and 4 are views illustrating positions (disposition depths) of a plurality of sensors in the outsole of FIG. 1.
Figure 4:
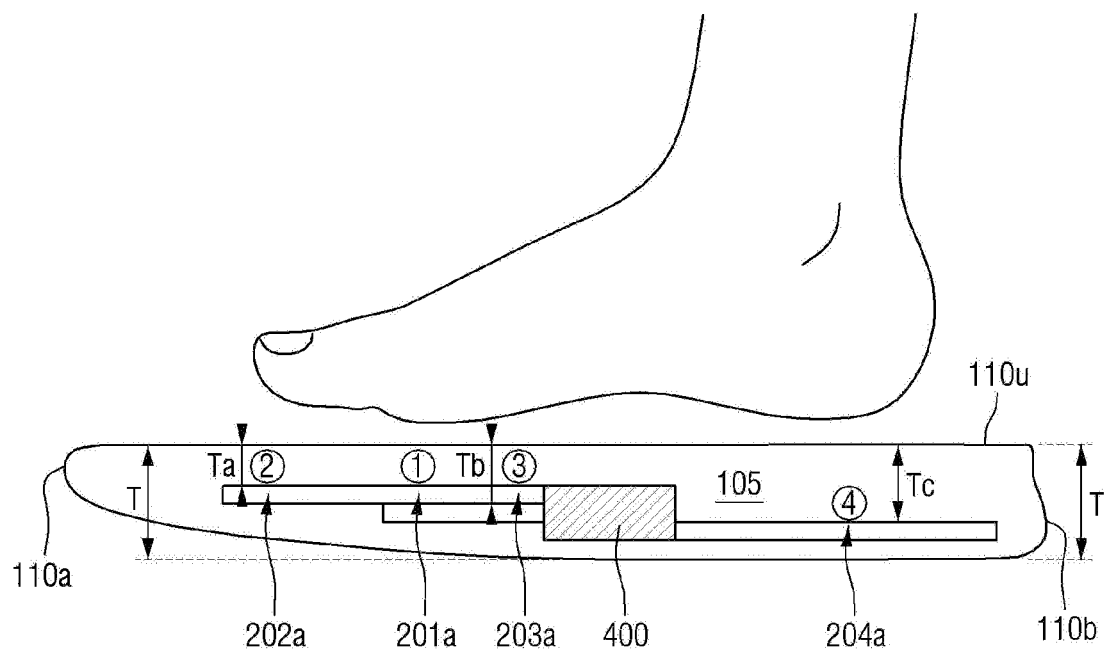

FIGS. 3 and 4 are views illustrating positions (disposition depths) of the plurality of sensors in the outsole of FIG. 1.

First, referring to FIG. 3, the plurality of sensors 201a, 202a, 203a, and 204a are embedded in the outsole. The plurality of sensors 201a, 202a, 203a, and 204a may be arranged to sense properties of each of parts of a user's foot (that is, toes, a ball of the foot, a heel of the foot, and the like).

For example, a first sensor 201a and a third sensor 203a may correspond to the ball of the foot, a second sensor 202a may correspond to the toes of the foot (particularly, a big toe), and a fourth sensor 204a may correspond to the heel of the foot. Here, the number and positions of the plurality of sensors 201a, 202a, 203a, and 204a may change according to a design. For example, the number of sensors 201a, 202a, 203a, and 204a may be five or more or three or less. Also, for example, the sensor 202a may be disposed in a position corresponding to a second toe or a third toe instead of the big toe, and for example, the sensors 201a and 203a may be arranged in positions corresponding to the mid-foot area. Also, the plurality of sensors 201a, 202a, 203a, and 204a may be film-type pressure sensors. However, depending on a design, other types of sensors may be arranged.

In the shoe according to some embodiments of the present invention, at least two of the plurality of sensors 201a, 202a, 203a, and 204a may be disposed at different depths.

In detail, closer to a front end 110a of the outsole 110, the sensors 201a, 202a, 203a, and 204a may be embedded to be closer to (shallower with respect to) a top surface 110u of the outsole 110. Also, toward the rear end 110b of the outsole 110, the sensors 201a, 202a, 203a, and 204a may be embedded to be farther from (deeper with respect to) the top surface 110u of the outsole 110.

Referring to FIGS. 3 and 4, the second sensor 202a may be installed at a disposition depth Ta, the first sensor 201a and the third sensor 203a may be installed at a disposition depth Tb, and the fourth sensor 204a may be installed at a disposition depth Tc. Here, the disposition depths Ta, Tb, and Tc refer to depths from the top surface 110u of the outsole 110.

The second sensor 202a is closer to the front end 110a of the outsole 110 than the fourth sensor 204a (that is, far from the rear end 110b of the outsole 110). Accordingly, the second sensor 202a is disposed to be shallower than the fourth sensor 204a. That is, the disposition depth Ta of the second sensor 202a is shallow in comparison to the disposition depth Tc of the fourth sensor 204a.

Also, the first sensor 201a and the third sensor 203a are farther from the front end 110a of the outsole 110 than the second sensor 202a and are farther from the rear end 110b of the outsole 110 than the fourth sensor 204a. Accordingly, the first sensor 201a and the third sensor 203a may be disposed to be deeper than the second sensor 202a and disposed to be shallower than the fourth sensor 204a. That is, the disposition depth Tb of the first sensor 201a and the third sensor 203a are deeper than the disposition depth Ta of the second sensor 202a and are shallower than the disposition depth Tc of the fourth sensor 204a.

Meanwhile, the first sensor 201a and the third sensor 203a are shown as being disposed at the same depth Tb in FIG. 4 but are not limited thereto. For example, according to a distance from the front end 110a of the outsole 110, a disposition depth of the first sensor 201a and a third disposition depth of the third sensor 203a may differ.

Also, the first sensor 201a to the fourth sensor 204a are embedded at depths of 10% or more and 70% or less from the top surface 110u of the outsole. Here, a depth shown as % is indicated on the basis of a thickness T of a thickest part (for example, the heel) of the outsole 110.

When the first sensor 201a to the fourth sensor 204a are embedded at depths of 0% or more and less than 10% from the top surface 110u of the outsole, the disposition depths Ta, Tb, and Tc are arranged too shallowly such that a consistent pressure value (or sensing value) is not extracted. Also, a pressure value is not extracted to be as much as an actually applied force. This will be described below in detail with reference to FIG. 5. Here, 0% means that a sensor is disposed to be exposed to the top surface 110u of the outsole 110.

Also, when the first sensor 201a to the fourth sensor 204a are embedded at depths of more than 70% and 100% or less from the top surface 110u of the outsole, the disposition depths Ta, Tb, and Tc are arranged too deep such that it is very difficult to obtain a pressure value with respect to a light weight. Also, when the sensors 201a, 202a, 203a, and 204a are too close to a bottom surface of the outsole 110, durability of the sensors 201a, 202a, 203a, and 204a decreases greatly. It will be described below in detail with reference to FIG. 6. Here, 100% means that a sensor is disposed to be exposed to the bottom surface of the outsole 110.

Accordingly, when the first sensor 201a to the fourth sensor 204a are embedded at depths of 10% or more and 70% or less from the top surface 110u of the outsole, it is possible to obtain an effective pressure value. It will be described below in detail with reference to FIG. 7.

The inventors of the present invention have derived a result as follows through a plurality of experiments. In a range of 10% or more and 70% or less, it is possible to obtain a most effective pressure value within a range of 10% or more and 40% or less, to obtain a considerably effective pressure value within a range of more than 40% and 60% or less, and to obtain an effective pressure value within a range of more than 60% and 70% or less. That is, pressure values are precisely obtained in an order of the range of 10% or more and 40% or less, the range of more than 40% and 60% or less, and the range of more than 60% and 70% or less.

In the range of 10% or more and 40% or less, the second sensor 202a may be installed at the disposition depth Ta of 10% or more and 20% or less, the first sensor 201a and the third sensor 203a may be installed at the disposition depth Tb of more than 20% and 30% or less, and the fourth sensor 204a may be installed at the disposition depth Tc of more than 30% and 40% or less. It will be described below in detail with reference to FIG. 8.

Meanwhile, the disposition depths Ta and Tb of the second sensor 202a and the first and third sensors 201a and 203a have been described as differing from each other but are not limited thereto. That is, depending on a design type, the disposition depths Ta and Tb may be the same. An exemplary embodiment thereof will be described in detail with reference to FIGS. 9 to 12. In consideration of a shoe shape and a foot shape, when the disposition depths Ta and Tb are the same, it is possible to easily embody the shoe.

Figure 5:
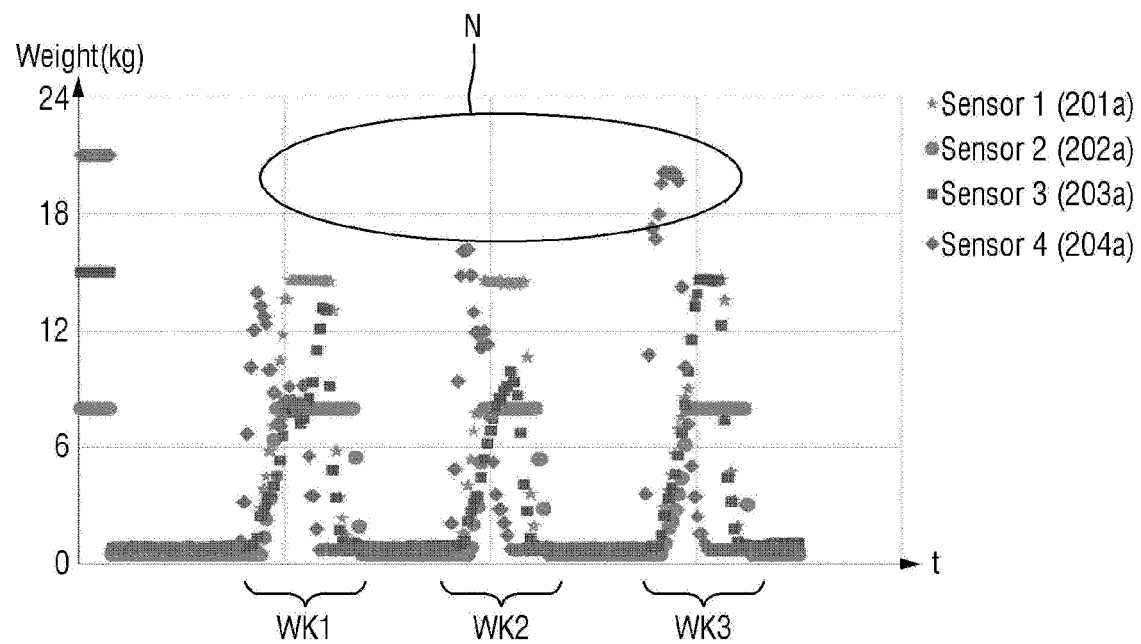
FIGS. 5 to 7 are graphs illustrating a relationship between a disposition depth and sensitivity of a sensor.
Figure 6:
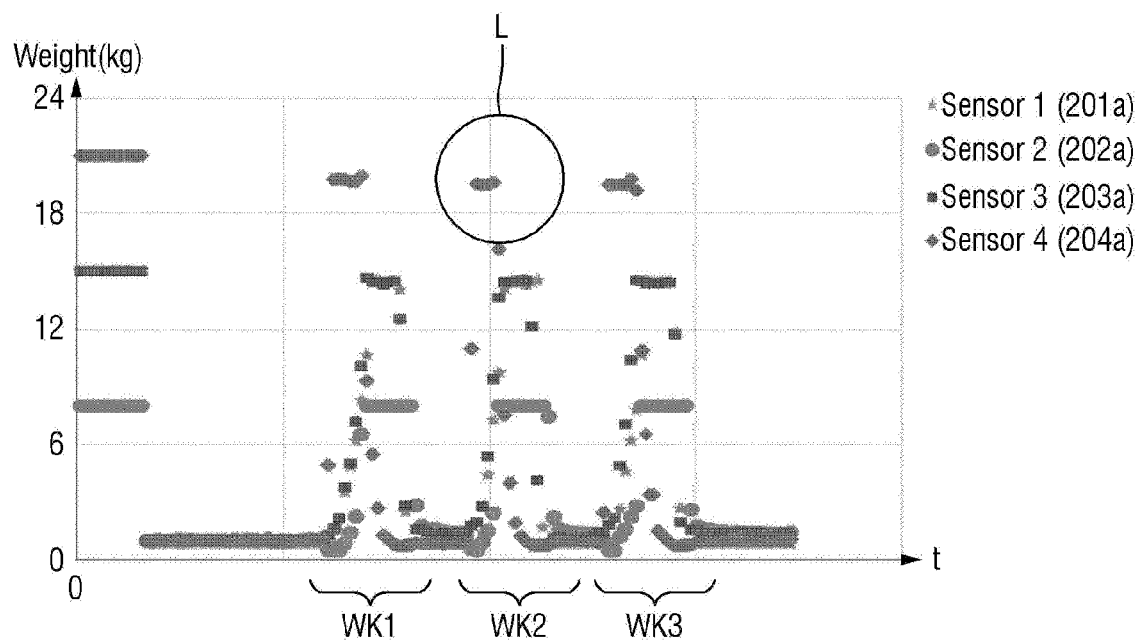
Figure 7:
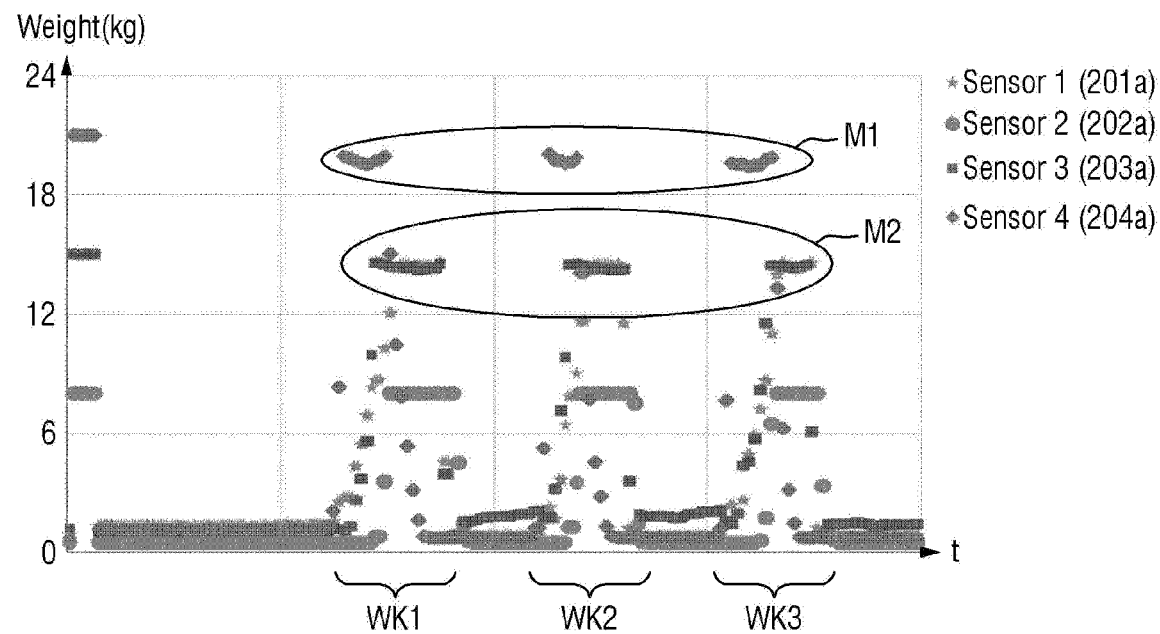

FIGS. 5 to 7 are views illustrating a relationship between a disposition depth and sensitivity of a sensor. FIGS. 5 to 7 illustrate test results. In FIGS. 5 to 7, an X-axis indicates time t and a Y-axis indicates a weight kg.

Test conditions of FIG. 5 are as follows. The first sensor 201a to the fourth sensor 204a were embedded at a depth of 0% or more and less than 10%. After the first sensor 201a to the fourth sensor 204a were embedded, pressure values of the first sensor 201a to the fourth sensor 204a during three consecutive walking cycles WK1 to WK3 were checked. During the three consecutive walking cycles WK1 to WK3, a maximum force of 21 kg was applied to the fourth sensor 204a, a maximum force of 15 kg was applied to the first sensor 201a and the third sensor 203a, and a maximum force of 8 kg was applied to the second sensor 202a.

As shown by a reference numeral N, it may be seen that although the maximum force of 21 kg was applied to the fourth sensor 204a, only about 15 kg was sensed. That is, it may be seen that the pressure value did not reach a level of force which was actually applied. Also, it may be seen that consistency among the pressure values of the first sensor 201a to the fourth sensor 204a was low.

Test conditions of FIG. 6 are as follows. The first sensor 201a to the fourth sensor 204a were embedded at a depth of more than 70% and 100% or less. After the first sensor 201a to the fourth sensor 204a were embedded, pressure values of the first sensor 201a to the fourth sensor 204a during three consecutive walking cycles WK1 to WK3 were checked. During the three consecutive walking cycles WK1 to WK3, a maximum force of 21 kg was applied to the fourth sensor 204a, a maximum force of 15 kg was applied to the first sensor 201a and the third sensor 203a, and a maximum force of 8 kg was applied to the second sensor 202a.

As shown by a reference numeral L, it may be seen that a sensing time (length) of the fourth sensor 204a was considerably shorter than a time for which a force was actually applied. It may be seen that the pressure values of the first sensor 201a and the third sensor 203a were not same. Although not additionally shown in the drawing, during the test, a plurality of cases were found in which sensing times (lengths) of the first sensor 201a and the third sensor 203a become considerably shorter.

Test conditions of FIG. 7 are as follows. The first sensor 201a to the fourth sensor 204a were embedded at a depth of 10% or more and 70% or less. After the first sensor 201a to the fourth sensor 204a were embedded, pressure values of the first sensor 201a to the fourth sensor 204a during three consecutive walking cycles WK1 to WK3 were checked. During the three consecutive walking cycles WK1 to WK3, a maximum force of 21 kg was applied to the fourth sensor 204a, a maximum force of 15 kg was applied to the first sensor 201a and the third sensor 203a, and a maximum force of 8 kg was applied to the second sensor 202a.

As shown by a reference numeral M1, it may be seen that the fourth sensor 204a sensed the pressure value to be as much as the applied force. The other sensors 201a, 201b, and 201c also sensed the pressure values to be as much as the applied forces. As shown by a reference numeral M2, it may be seen that the first sensor 201a and the third sensor 203a had sensing times (lengths) which were the same as actually applied times. As shown by a reference numeral M1, it may be seen that the fourth sensor 204a also had an adequate sensing time (length).

Figure 8:
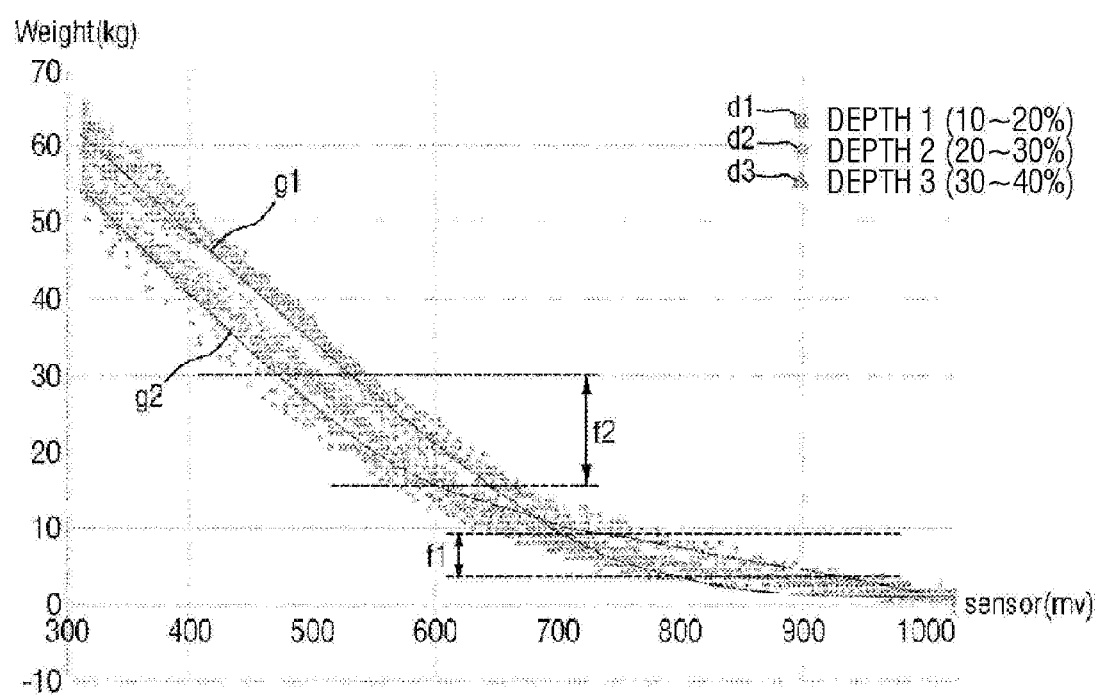
FIG. 8 is a graph illustrating a relationship between a disposition depth and sensitivity of a sensor.

FIG. 8 is a graph illustrating a relationship between a disposition depth and sensitivity of a sensor. FIG. 8 is a graph for detecting optimal values of the disposition depths of the first sensor 201a to the fourth sensor 204a. In FIG. 8, an X-axis indicates a voltage mV sensed by a sensor, and a Y-axis indicates a weight kg.

Referring to FIG. 8, a voltage, which was measured by a sensor while the sensor was disposed at the disposition depth Ta of 10% or more and 20% or less and then a weight kg was changed, is recorded as a quadrangular dot (or an orange-colored dot) d1. The voltage was measured a plurality of times for each weight kg.

A voltage, which was measured by the sensor while the sensor was disposed at the disposition depth Tb of more than 20% and 30% or less and then the weight kg was changed, is recorded as a circular dot (or a gray-colored dot) d2. The voltage was measured a plurality of times for each weight kg.

A voltage, which was measured by the sensor while the sensor was disposed at the disposition depth Tc of more than 30% and 40% or less and then the weight kg was changed, is recorded as a triangular dot (or a sky blue-colored dot) d3. The voltage was measured a plurality of times for each weight kg.

A line g1 connects average values of the triangular dots d3, and a line g2 connects averages values of the quadrangular dots d1.

First, when seeing the quadrangular dots d1 and the triangular dots d3, it may be seen that the quadrangular dots d1 are marked at a maximum of about 55 kg and the triangular dots d3 are marked at a maximum of about 68 kg. That is, it may be seen that a heavier weight (force) is measurable at the deep disposition depth Tc and a relatively lighter weight (force) is measurable at the shallow disposition depth Ta (refer to the quadrangular dots d1). That is, it may be seen that a heavier weight (force) is measurable when a disposition depth becomes deeper.

Additionally, when the line g1 and the line g2 in a first weight section f1 are compared with each other, it may be seen that the line g2 is more straight, or linear, than the line g1.

On the other hand, when the line g1 and the line g2 are compared with each other in a second weight section f2, which is heavier than the first weight section f1, it may be seen that the line g1 has more straightness or linearity than the line g2. That is, it may be seen that linearity is shown with respect to a heavier weight (force) as a disposition depth becomes deeper.

That is, it may be seen that linearity is shown with respect to a lighter weight (force) as a disposition depth becomes shallower.

Accordingly, the fourth sensor 204a for measuring a heavier weight is disposed deeper than the first sensor 201a to the third sensor 203a. The second sensor 202a for measuring a lighter weight is disposed shallower than the first sensor 201a, the third sensor 203a, and the fourth sensor 204a. As a result thereof, the second sensor 202a may be installed at the disposition depth Ta of 10% or more and 20% or less, the first sensor 201a and the third sensor 203a may be installed at the disposition depth Tb of more than 20% and 30% or less, and the fourth sensor 204a may be installed at the disposition depth Tc of more than 30% and 40% or less.

Embodiments of the sensing system will be described with reference to FIGS. 9 to 12. FIGS. 9 to 12 exemplarily illustrate a case in which the disposition depths Ta and Tb of the second sensor 202a and the first and third sensors 201a and 203a are the same.

Figure 9:
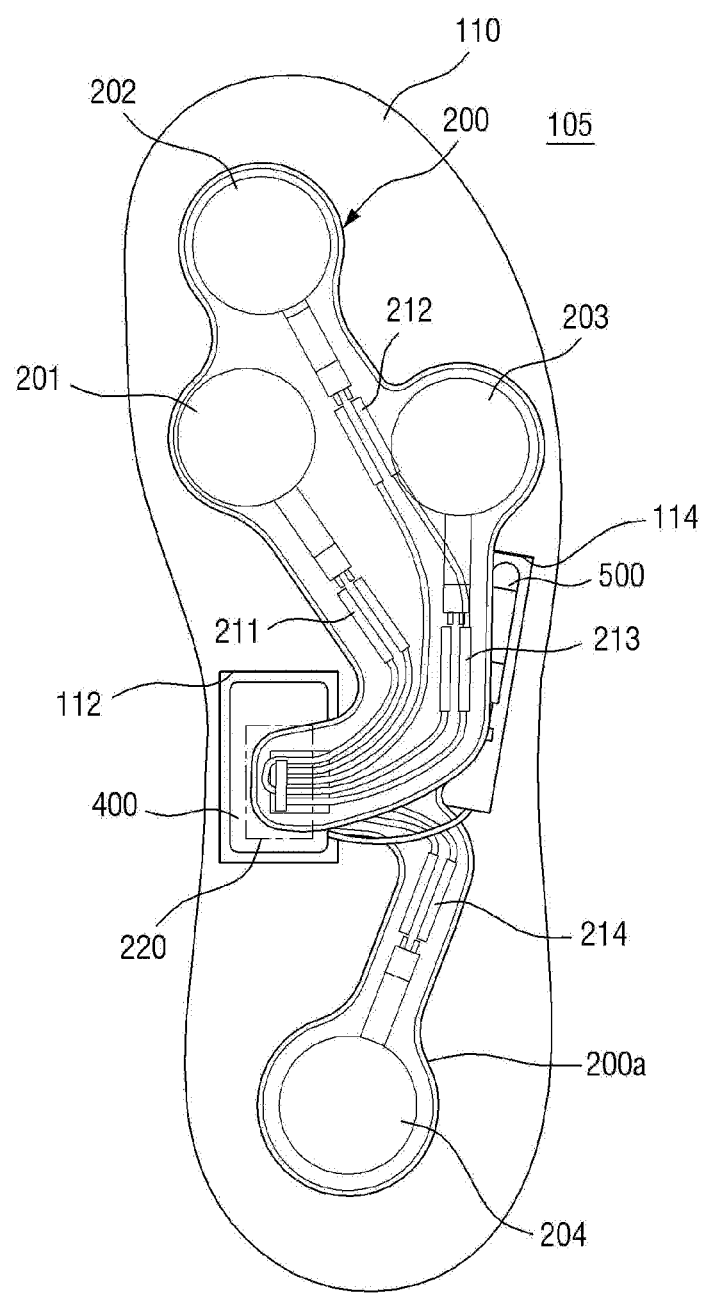
FIGS. 9 to 12 are views illustrating embodiments of a sensing system.
Figure 10:
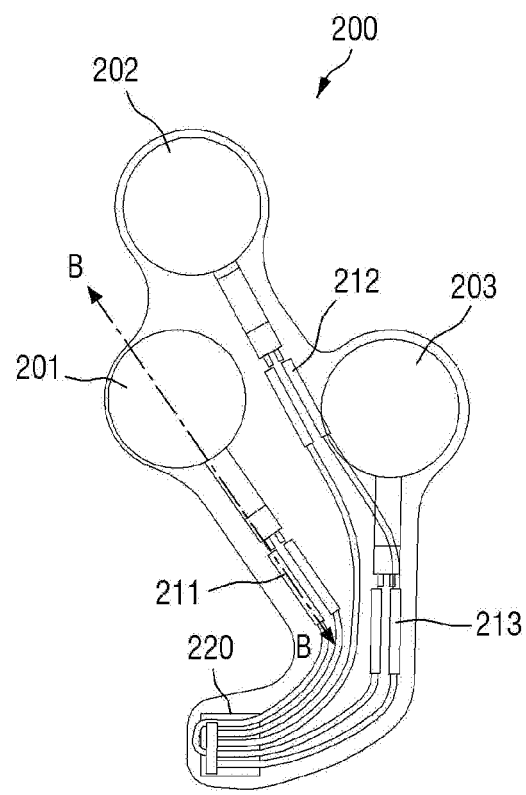
Figure 11:
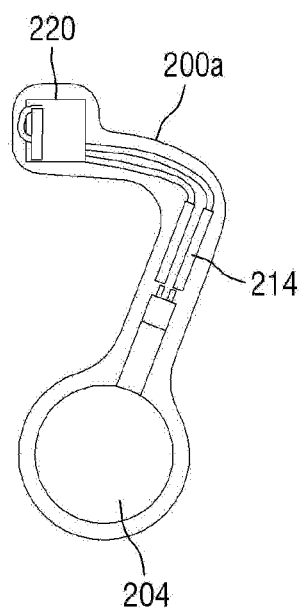
Figure 12:
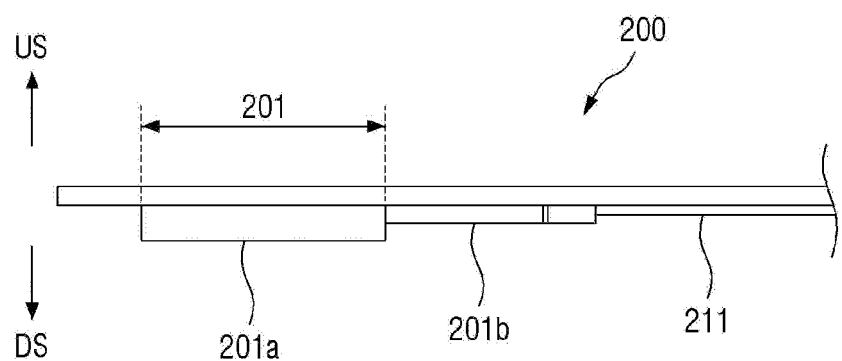

FIG. 9 is a view illustrating a sensing system which is completely embedded in the outsole of FIG. 1. FIG. 10 illustrates a first flexible circuit board of FIG. 9. FIG. 11 illustrates a second flexible circuit board of FIG. 9. FIG. 12 is a cross-sectional view taken along a line B-B of FIG. 10.

First, referring to FIGS. 9 to 11, the sensing system 105 may include a first flexible circuit board 200, a second flexible circuit board 200a, a control module 400, an antenna 500, and the like.

The first flexible circuit board 200 and the second flexible circuit board 200a are separated from each other. For example, the first flexible circuit board 200 may be connected to a top surface of the control module 400 and the second flexible circuit board 200a may be connected to a rear surface of the control module 400 but the present invention is not limited thereto.

The first flexible circuit board 200 includes a plurality of sensing areas 201, 202, and 203, in which the plurality of sensors 201a, 202a, and 203a are installable, and wires 211, 212, and 213, which are connected to the plurality of sensors. The second flexible circuit board 200a includes a plurality of sensing areas 204 in which at least one sensor 204a is installable and a wire 214 is connected to the at least one sensor.

Among the sensing areas 201, 202, 203, and 204, a first sensing area 201 and a third sensing area 203 may correspond to a ball of a foot, the second sensing area 202 may correspond to a big toe of the foot, and the fourth sensing area 204 may correspond to a heel of the foot. Here, the number and positions of the plurality of sensing areas 201, 202, 203, and 204 may change according to a design. For example, the number of sensing areas 201, 202, 203, and 204 may be five or more or three or less. Also, the sensing areas 201, 202, 203, and 204 may be arranged in positions corresponding to a second toe or a third toe instead of the big toe and may correspond to a mid-foot area. Hereinafter, one of the sensors 201a, 202a, 203a, and 204a is described as being disposed in each of the sensing areas 201, 202, 203, and 204 but the present invention is not limited thereto. That is, instead of one sensor, two or more sensors may be arranged in each of the sensing areas 201, 202, 203, and 204. Also, in the shoe according to some embodiments of the present invention, the sensors 201a, 202a, 203a, and 204a may be film-type pressure sensors. Depending on a design, another shape of sensors may be disposed.

Disposition depths of the plurality of sensors 201a, 202a, 203a, and 204a may be positions which have been described with reference to FIGS. 3 to 8. The plurality of sensors 201a, 202a, 203a, and 204a are embedded at depths of 10% or more and 70% or less. For example, the second sensor 202a may be installed at the disposition depth Ta of 10% or more and 20% or less, the first sensor 201a and the third sensor 203a may be installed at the disposition depth Tb of more than 20% and 30% or less, and the fourth sensor 204a may be installed at the disposition depth Tc of more than 30% and 40% or less.

The wires 211, 212, 213, and 214 may start from a connection area 220 and may diverge toward the sensing areas 201, 202, 203, and 204.

For example, the wires 211, 212, 213, and 214, as shown in the drawings, may have a reverse C shape or a right side of brackets, that is, a "１" shape. That is, the wires 211, 212, 213, and 214 may start from the connection area 220 and deviate from an outside of the shoe to reach the sensing areas 201, 202, 203, and 204. Due to the above shape, the wires 211, 212, 213, and 214 may be stably collected in the connection area 220, and the wires 211, 212, 213, and 214 may be prevented from being broken.

Here, the wires 211, 212, 213, and 214 may be electrically connected to the control module 400 through the connection area 220.

Although the connection area 220 will be described below, the connection area 220 may be formed inside the arch area AR of the shoe.

Also, as shown in FIG. 12, for example, the sensor 201a may be disposed in a downward direction DS of, for example, the sensing area 201 of the first flexible circuit board 200. For example, a wire 201b from the sensor 201a may be directly connected to the wire 211 of a wire area. The wires 201b and 211 may be arranged in the downward direction DS. Here, an upward direction US is a direction in which a foot of a user of the shoe 100 is present and the downward direction DS is opposite to the upward direction US and toward the ground. As described above, the wires 201b and 211 and the sensor 201a face the downward direction DS. Additionally, since a support plate is present below the first flexible circuit board 200, durability of the wires 201b and 211 and the sensor 201a may increase.

Since the sensing system 105 is formed to be completely embedded in the outsole 110, for example, when the wires 201b and 211 face the upward direction US, the wires 201b and 211 come into direct contact with the outsole 110. In this case, friction occurs between the wires 201b and 211 and the outsole 110 such that the wires 201b and 211 may be easily broken. On the other hand, when the wires 201b and 211 face the support plate 300, a possibility, in which a phenomenon of being broken occurs, decreases.

For example, a disposition direction of the sensor 201a of the second flexible circuit board 200a may be the same as a disposition direction of, for example, the sensor 204a of the first flexible circuit board 200. That is, for example, the sensor 204a may be disposed in the downward direction DS of, for example, the sensing area 204 of the second flexible circuit board 200a.

Although not particularly shown in the drawing, support plates may be disposed below the first flexible circuit board 200 and the second flexible circuit board 200a. The support plates increase sensing sensitivities of the sensors 201a, 202a, 203a, and 204a.

When a user walks, runs, or exercises, a foot of the user steps on, for example, the sensor 201a (the film-type pressure sensor). However, since the sensor 201a is embedded in the outsole 110, when the support plate is not present, the sensor 201a may directly push the outsole 110 when the foot of the user steps on the sensor 201a. However, when the outsole 110 is formed of a soft material capable of preventing a shock (for example, rubber, silicone, and the like), the sensor 20a meets the soft material. Accordingly, the sensing sensitivity of the sensor 201a decreases. Accordingly, below the sensing areas 201, 202, 203, and 204 of the flexible circuit board 200, the support plate formed of a material having higher strength than strength of the outsole 110 is installed. Accordingly, when the foot of the user pushes the sensor 201a, the sensor 201a comes into direct contact with the support plate instead of the soft material. Accordingly, the sensing sensitivity of the sensor 201a may increase. The support plate may have strength higher than strength of the flexible circuit board 200.

Figure 13:
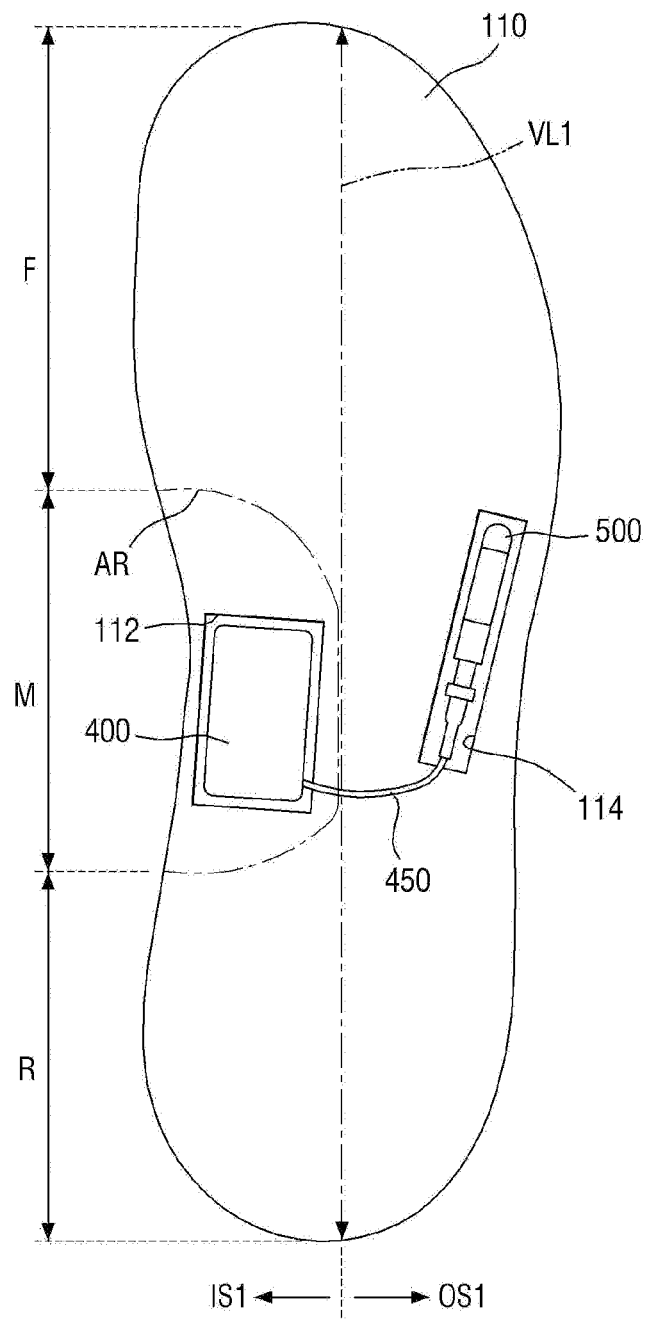
FIG. 13 is a view illustrating a control module and an antenna of FIG. 9.

FIG. 13 is a view illustrating the control module and the antenna of FIG. 9.

Referring to FIG. 13, the control module 400 may be disposed to correspond to the inside of the arch area AR.

As described above, the arch area AR may be a part corresponding to an arch area of the foot. The arch of the foot performs a function of stably maintaining posture while standing, a function of absorbing a shock by sensing an excessive force of a weight, and the like. The arch of the foot is a position which is a dented position and receives a least amount of weight. Accordingly, in the shoe according to some embodiments of the present invention, the control module 400 is disposed on an inside IS1 of the arch area AR such that durability of the control module 400 may be provided.

As described above, the outsole 110 includes the forefoot area F, the mid-foot area M, and the rear foot area R. In detail, the control module 400 may be disposed on the inside IS1 on the basis of a first virtual line VL1 which connects both ends of the outsole 110 in a longitudinal direction thereof in the mid-foot area M.

Also, the control module 400 may be mounted in a first trench 112 of the outsole 110. The control module 400 may include a circuit board connected to the wires 211, 212, 213, and 214 through the connection area 220 (refer to FIG. 9) and at least one chip and/or passive element installed on the circuit board. The control module 400 may be in, for example, a case. A bottom surface of the case may have a curved shape to surround the circuit board. The curved shape may protect the circuit board, the chip, the passive element, and the like from shocks.

On the other hand, the antenna 500 may be disposed on an outside OS1 on the basis of the first virtual line VL1. The antenna 500 may be mounted in a second trench 114 of the outsole 110. The control module 400 and the antenna 500 are connected through a wire 450, and an additional trench on which the wire 450 is mounted may be present in the outsole 110.

Here, depending on a position of the antenna 500 in the outsole 110, emissivity (or an emission rate) of the antenna 500 may change.

As the antenna 500 moves toward the inside IS1, since a signal generated by the control module 400 is hidden by the outsole, the signal is hardly transmitted to an external device. On the other hand, as the antenna 500 becomes closer to the outside, the signal generated by the control module 400 is easily transmitted to the external device. Also, as the antenna 500 becomes closer to the innermost side other than the outermost side, emissivity may decrease. As an example, a left foot is located in an inward direction of a right foot. Accordingly, the presence and movement of the left foot may decrease the emissivity of the signal generated by the control module 400.

Accordingly, in the shoe according to some embodiments of the present invention, the antenna 500 is disposed on the outside OS1 of the first virtual line VL1 and disposed to be maximally close to the outermost side. Simply in order to completely embed the antenna 500 in the outsole 110, for example, the antenna 500 may be disposed inward 2 mm to 5 mm from the outermost side.

Figure 14:
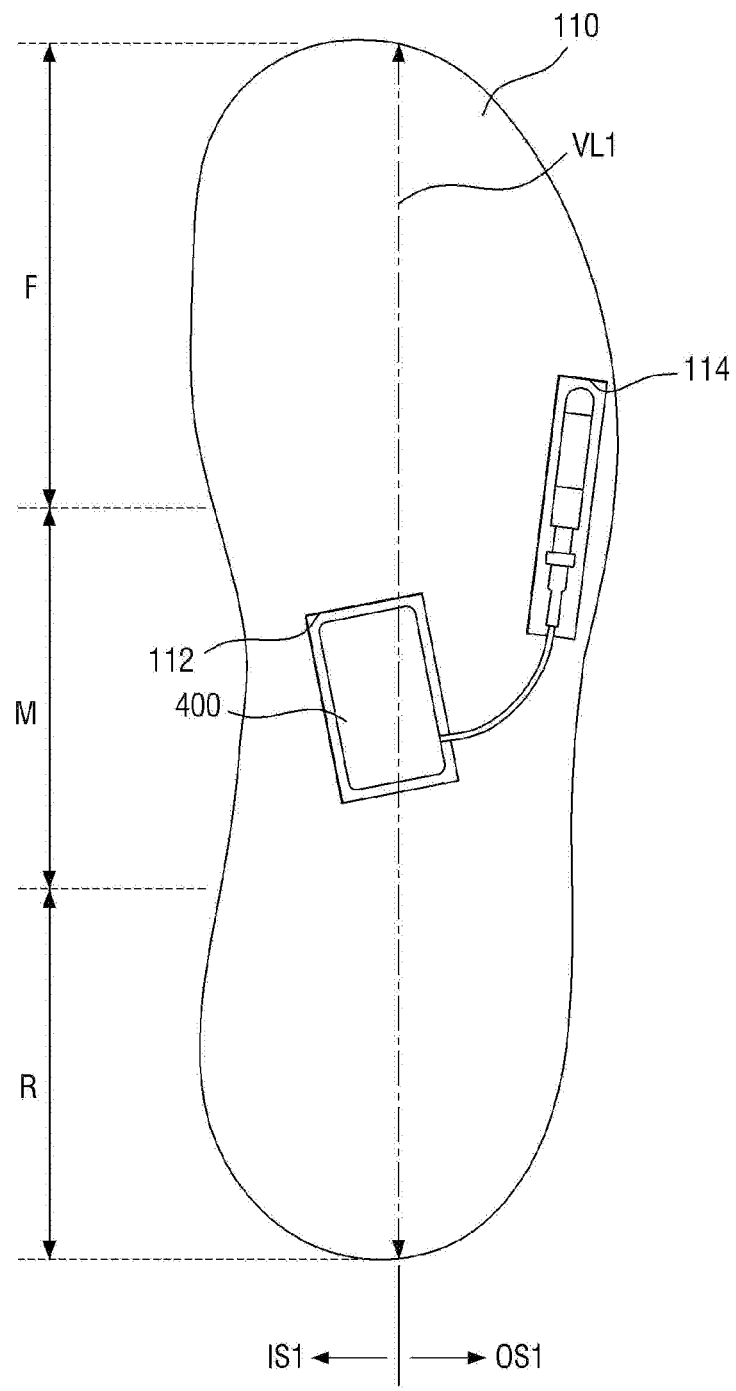
FIG. 14 is a view illustrating the control module and the antenna of FIG. 9.

FIG. 14 is a view illustrating the control module and the antenna of FIG. 9. For convenience of description, only points different from FIG. 13 will be described.

Referring to FIG. 14, the entire control module 400 may not be in the arch area AR. For example, 50% or more of the control module 400 may be disposed in the arch area AR. As shown in the drawing, 60% or more, in more detail, 70% or more, of the control module 400 may be disposed in the arch area AR.

Figure 15:
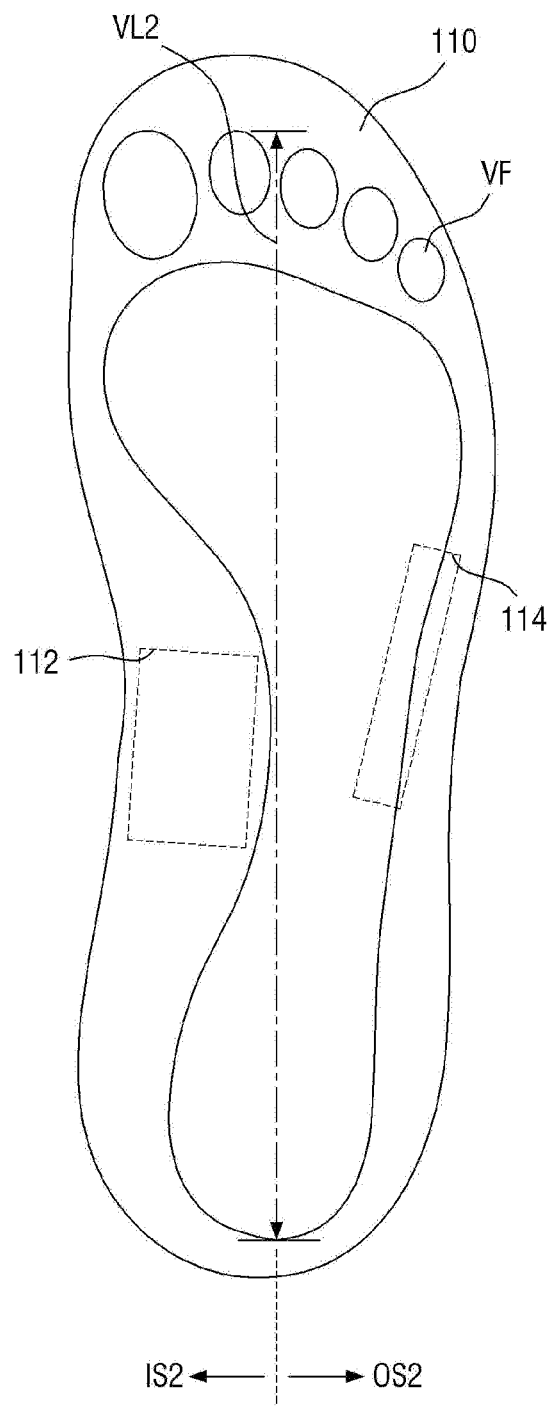
FIG. 15 is a view illustrating the control module and the antenna of FIG. 9.

FIG. 15 is a view illustrating the control module and the antenna of FIG. 9.

Referring to FIG. 15, a position of the control module 400 will be described in another way as follows. That is, the control module 400 may be disposed in the mid-foot area on an inside 102 on the basis of a second virtual line VL2 which connects a second toe to an end of a foot, and the antenna 500 may be disposed on an outside OS2 on the basis of the second virtual line VL2.

Figure 16:
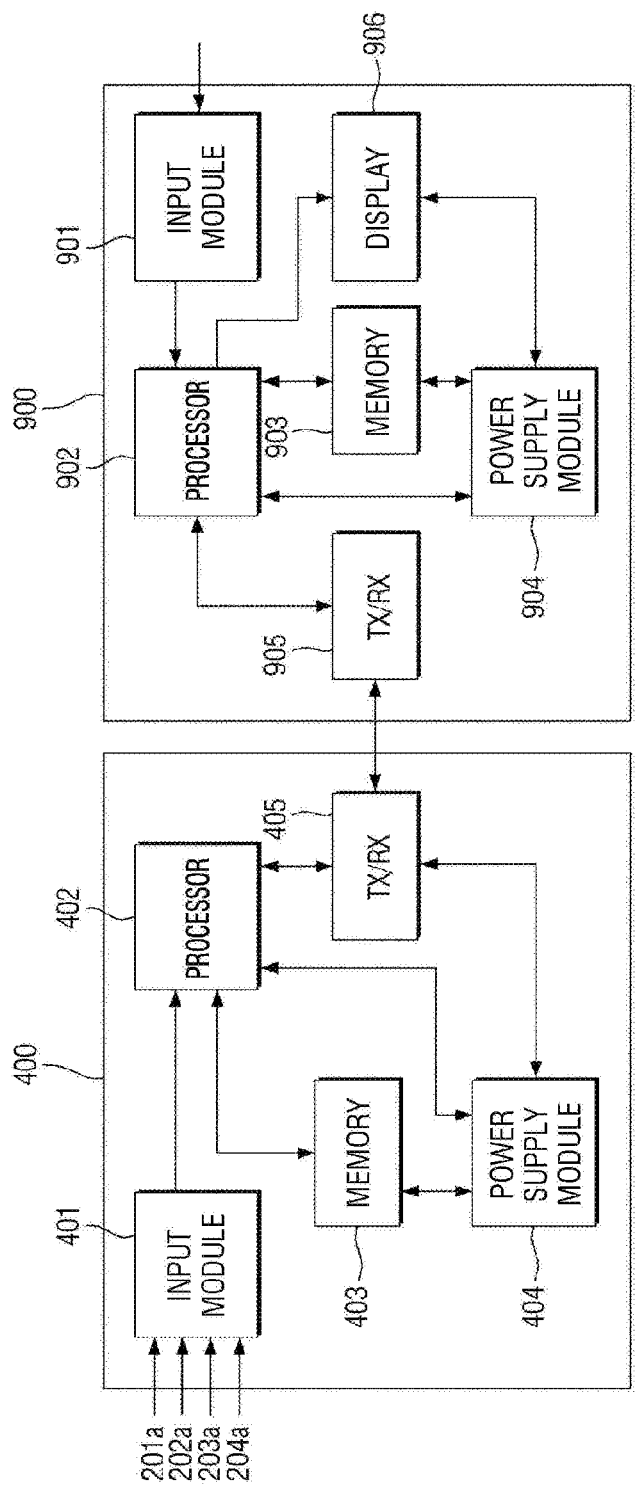
FIG. 16 is a view illustrating a relationship between the shoe and an external device according to some embodiments of the present invention.

FIG. 16 is a view illustrating a relationship between the shoe and an external device according to some embodiments of the present invention. A configuration of the shoe (the control module 400) and a configuration of the external device shown in FIG. 16 are examples and the present invention is not limited thereto.

Referring to FIG. 16, the control module 400 may include an input module 401, a processor 402, a memory 403, a power supply module 404, a transmission and reception module 405, and the like. Each module therein may be separately housed or some modules may be housed as one.

The input module 401 receives a plurality of sensing values provided by the plurality of sensors 201a to 204a. As described above, the plurality of sensors 201a to 204a may be film-type pressure sensors.

The processor 402 processes the plurality of sensing values which are input thereto. For example, the processor 402 may convert the plurality of sensing values into a data format adequate for being stored in the memory 403 or may match measuring times with the sensing values. The processor 402 controls the memory 403, the power supply module 404, and the transmission and reception module 405.

The memory 403 may store the plurality of sensing values according to a time or may store signals processed by the processor 402.

The power supply module 404 may supply power to the processor 402, the memory 403, the transmission and reception module 405, and the like.

Unlike the drawing, an additional sensor (not shown) may be installed in the shoe 100. For example, the additional sensor may sense pedometer type velocity and/or distance information, other velocity and/or distance data sensor information, a temperature, an altitude, atmospheric pressure, humidity, global positioning system (GPS) data, accelerator type output or data, a heat rate, a pulse, a blood pressure, electrocardiogram (EKG) data, electroencephalogram (EEG) data, angular orientation (a gyroscope-based sensor and the like), data related to a change in the angular orientation, and the like. Otherwise, the additional sensor may sense data or information related to a wide variety of different types of parameters such as use of a shoe product or physical or biological data related to a user.

The control module 400 may communicate with an external device 900 with respect to sensing values or processed data through the transmission and reception module 405.

The external device 900 may be a computing system (for example, a desktop personal computer (PC), a smart phone, a tablet, a pad, a server, and the like) but a type thereof is not limited. The external device 900 may include an input module 901, a processor 902, a memory 903, a power supply module 904, a transmission and reception module 905, a display module 906, and the like.

The input module 901 may receive instructions/data and the like from a user.

The transmission and reception module 905 may receive sensing values or processed data from the shoe 100. Also, signals/data may be provided by other components in addition to the shoe 100.

The processor 902 processes the signals/data provided from the transmission and reception module 905. For example, depending on time, an operation of matching the sensing values with video signals (for example, video signals obtained by measuring a movement (motion) performed by using a camera while the shoe is being worn) may be performed.

Also, the processor 902 may generate a variety of calculation values on the basis of the sensing values provided by the plurality of sensors 201a, 202a, 203a, and 204a. Also, the processor 902 matches the calculation values with the video signals according to a time. An image displayed by the matched calculation values and video signals will be described below with reference to FIGS. 21 to 25.

R1, R2, R3, and R4 refer to sensing values sensed by the sensors 201a, 202a, 203a, and 204a installed in the sensing areas 201, 202, 203, and 204 (refer to FIG. 2) of a right shoe. Likewise, L1, L2, L3, and L4 refer to sensing values sensed by sensors installed in sensing areas of a left shoe. For example, Ri (i=1, 2, 3, 4) and Li (i=1, 2, 3, 4) are sensing values obtained by the sensors installed in positions which are symmetrical to each other.

Examples of the calculation values generated by the processor 902 are as follows.

$$RF = R1 + R2 + R3$$

$$RB = R4$$

$$RA = RF + RB = R1 + R2 + R3 + R4$$

$$LF = L1 + L2 + L3$$

$$LB = L4$$

$$LA = LF + LB = L1 + L2 + L3 + L4$$

Here, RF is a sum of sensing values sensed at a front of the right shoe, and RB is a sum of sensing values sensed at a back of the right shoe. RA is a sum of sensing values sensed in an entirety of the right shoe.

Here, LF is a sum of sensing values sensed at a front of the left shoe, and LB is a sum of sensing values sensed at a back of the left shoe. LA is a sum of sensing values sensed in an entirety of the left shoe.

$$FRT = RF + LF = R1 + R2 + R3 + L1 + L2 + L3$$

$$BCK = RB + LB = R4 + L4$$

Here, FRT is a sum of sensing values sensed at the fronts of the left shoe and the right shoe, and BCK indicates a sum of sensing values sensed at the backs of the left shoe and the right shoe.

Meanwhile, the above-described calculation values RF, RB, RA, LF, LB, LA, FRT, and BCK are described as being calculated using a simple arithmetic sum but the present invention is not limited thereto. That is, a weighted sum may be used. For example, more weights may be given to R1 and L1 than R3 and L3 so as to calculate RF, RB, RA, LF, LB, LA, FRT, BCK, and the like.

Also, the processor 902 may calculate a variety of ratio forms of calculation values R_RF_LF1, R_RF_LF2, R_RB_LB1, R_RB_LB2, R_RA_LA1, R_RA_LA2, R_FRT_BCK1, R_FRT_BCK2 by using the calculated calculation values RF, RB, RA, LF, LB, LA, FRT, BCK, and the like.

$$R\_RF\_LF1 = RF:LF$$

$$R\_RF\_LF2 = (RF/FRT)*100:(LF/FRT)*100$$

$$R\_RB\_LB1 = RB:LB$$

$$R\_RB\_LB2 = (RB/BCK)*100:(LB/BCK)*100$$

$$R\_RA\_LA1 = RA:LA$$

$$R\_RA\_LA2 = (RA/(RA+LA))*100:(LA/(RA+LA))*100$$

$$R\_FRT\_BCK1 = FRT:BCK$$

$$R\_FRT\_BCK2 = (FRT/(FRT+BCK))*100:(BCK/(FRT+BCK))*100$$

Here, R_RF_LF1 is a ratio between a sensing value sensed at a front of a right shoe and a sensing value sensed at a front of a left shoe. R_RF_LF2 is a value obtained by converting R_RF_LF1 on the basis of 100%. For example, when R_RF_LF1=33:11 (or shown as 3:1), it may become R_RF_LF1=75:25.

Similarly, R_RB_LB1 is a ratio between a sensing value sensed at a back of a right shoe and a sensing value sensed at a back of a left shoe. R_RB_LB2 is a value obtained by converting R_RB_LB1 on the basis of 100%.

Similarly, R_RA_LA1 is a ratio between a sum of sensing values sensed at a right shoe and a sum of sensing values sensed at a left shoe. R_RA_LA2 is a value obtained by converting R_RA_LA1 on the basis of 100%.

Similarly, R_FRT_BCK1 is a ratio between a sum of sensing values sensed at fronts of right/left shoes and a sum of sensing values sensed at backs of right/left shoes. R_FRT_ BCK2 is a value obtained by converting R_FRT_BCK1 on the basis of 100%.

The calculation values which are generated as described above may be externally shown through the display module 906. The generated calculation values may be shown as is or may be shown as a variety of forms of graphics (or in a user interface (UI) form) through the display module 906. An example of the UI form will be described below in detail with reference to FIGS. 17 to 25.

Also, the processor 902 controls the memory 903, the power supply module 904, the transmission and reception module 905, the display module 906, and the like. The memory 903 stores signals/data provided by the processor 902. The power supply module 904 supplies power to the processor 902, the memory 903, the display module 906, and the like. The display module 906 externally shows signals/data generated by the processor 902.

FIGS. 17 to 20 are exemplary graphs displaying generated calculation values. FIGS. 17 to 20 merely illustrate examples of displaying the generated calculation values, and the calculation values may be embodied in another form.

Figure 17:
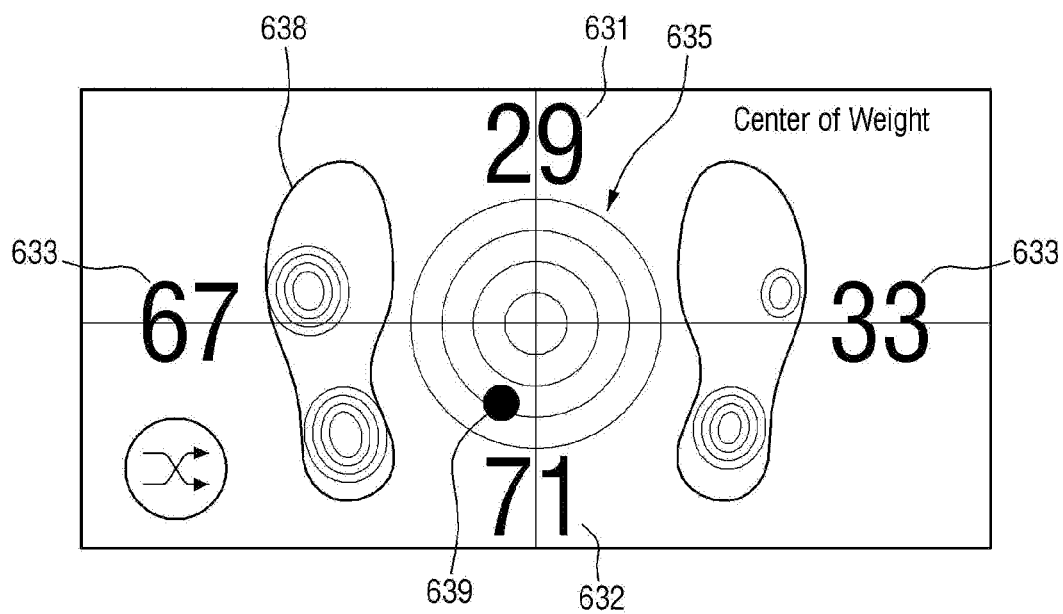
FIGS. 17 to 20 are exemplary graphs displaying generated calculation values.

FIG. 17 is a graph illustrating a left shoe model, a right shoe model, and a center of weight (COW) at the same time.

Referring to FIG. 17, the sensing values L1, L2, L3, and L4 sensed by the plurality of sensors installed in the left shoe are intuitively shown in a left shoe model 636. In a right shoe model 635, the sensing values R1, R2, R3, and R4 sensed by the plurality of sensors installed in the right shoe are intuitively shown. High and low sensing values may be shown in a variety of methods such as color/brightness/chroma/isobaric line and the like.

Reference numerals 631 and 632 refer to R_FRT_BCK2. That is, sensing values 631 sensed at fronts of right/left shoes are 29, and sensing values 632 sensed at backs of right/left shoes are 71.

Reference numerals 633 and 634 refer to R_RA_LA2. That is, the sensing value 633 sensed at a left shoe is 67, and the sensing value 634 sensed at a right shoe is 33.

Also, COW indicates where a center of gravity is for a user who wears shoes. That is, COW may be shown by marking a point 639 on a virtual plane 638. COW may be determined using a value of R_FRT_BCK2, R_RA_LA2.

Figure 18:
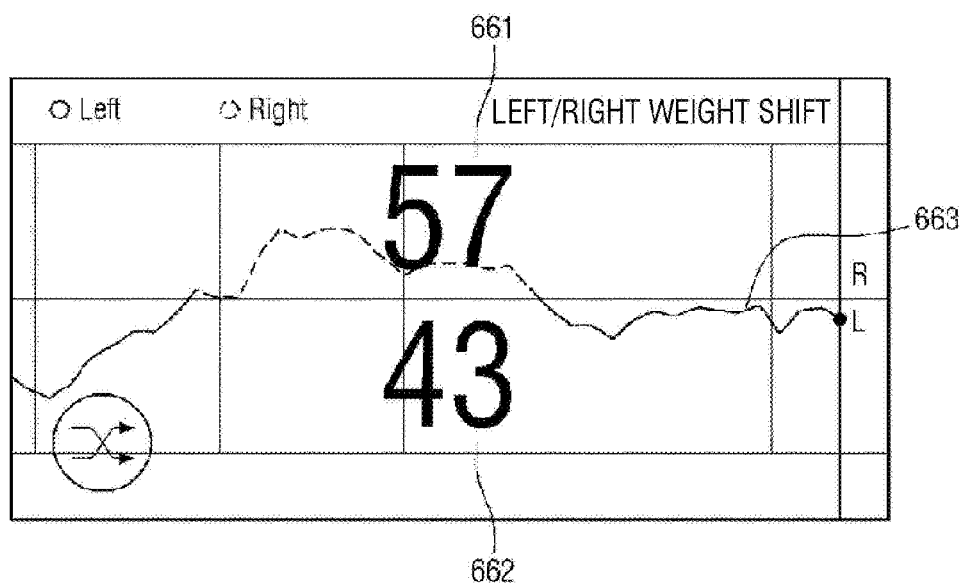

FIG. 18 is a screen for displaying a change of a calculation value R_RA_LA2 according to a time.

Referring to FIG. 18, the change of the calculation value R_RA_LA2 according to a time is shown as a line 663 in which rocking leftward and rightward may be seen.

Reference numerals 661 and 662 show the calculation values R_RA_LA2 as numbers. The sensing value 662 sensed at a left shoe is 43, the sensing value 661 sensed at a right shoe is 57. The calculation value R_RA_LA2 at a position on a line 663 which is designated by a user is shown as the reference numerals 661 and 662. When the user does not designate the position on the line 663, a calculation value R_RA_LA2 at a current time (or a current state) may be shown or a calculation value R_RA_LA2 at a final use time of the shoe may be shown. Otherwise, according to a selection of the user, a number which indicates the calculation value R_RA_LA2 may not be shown (that is, may be optional).

Figure 19:
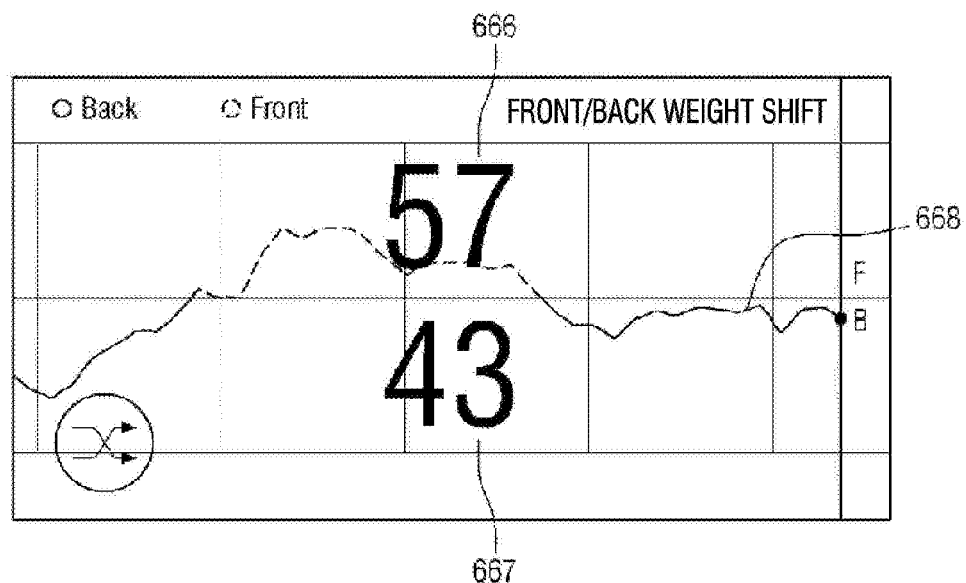

FIG. 19 is a screen for displaying a change of a calculation value R_FRT_BCK2 according to a time.

Referring to FIG. 19, the change of the calculation value R_RA_LA2 according to a change in time is shown as a line 668 in which rocking leftward and rightward according to a time may be seen.

Reference numerals 666 and 667 show the calculation values R_FRT_BCK2 as numbers. The sensing value 666 sensed at fronts of right/left shoes is 57, the sensing value 667 sensed at backs of right/left shoes is 43. The calculation value R_FRT_BCK2 at a position on a line 668 which is designated by a user is shown as the reference numerals 666 and 667. When the user does not designate the position on the line 668, a calculation value R_FRT_BCK2 at a current time (or a current state) may be shown or a calculation value R_FRT_BCK2 at a final use time of the shoe may be shown. Otherwise, according to a selection of the user, a number which indicates the calculation value R_FRT_BCK2 may not be shown (that is, may be optional).

Figure 20:
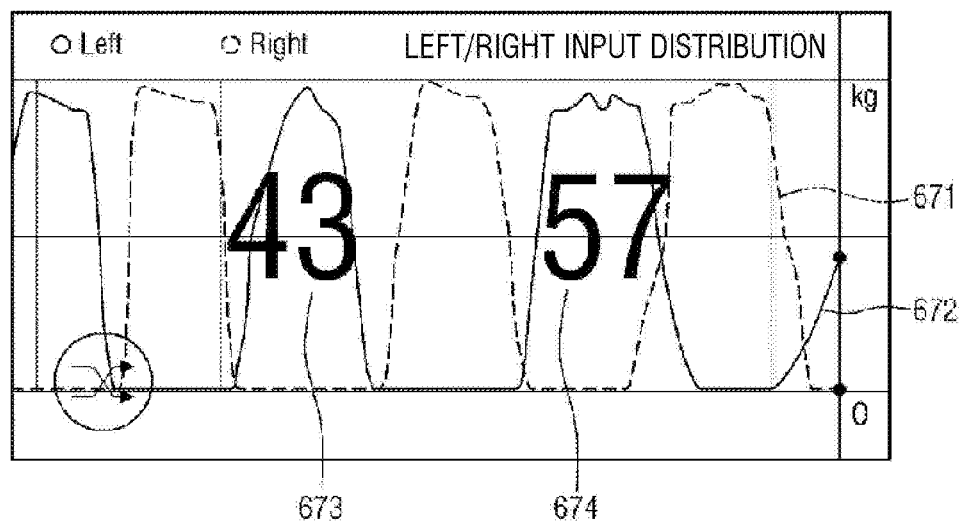

FIG. 20 is a screen for displaying a change of calculation values RA and LA according to a time.

Referring to FIG. 20, changes in the calculation values RA and LA according to a time are shown as lines 671 and 672 such that it may be seen whether bottoms of the right/left shoes come into contact with the ground according to a time.

The contact of the right shoe may be seen through the reference numeral 671, and the contact of the left shoe may be seen through the reference numeral 672.

Figure 21:
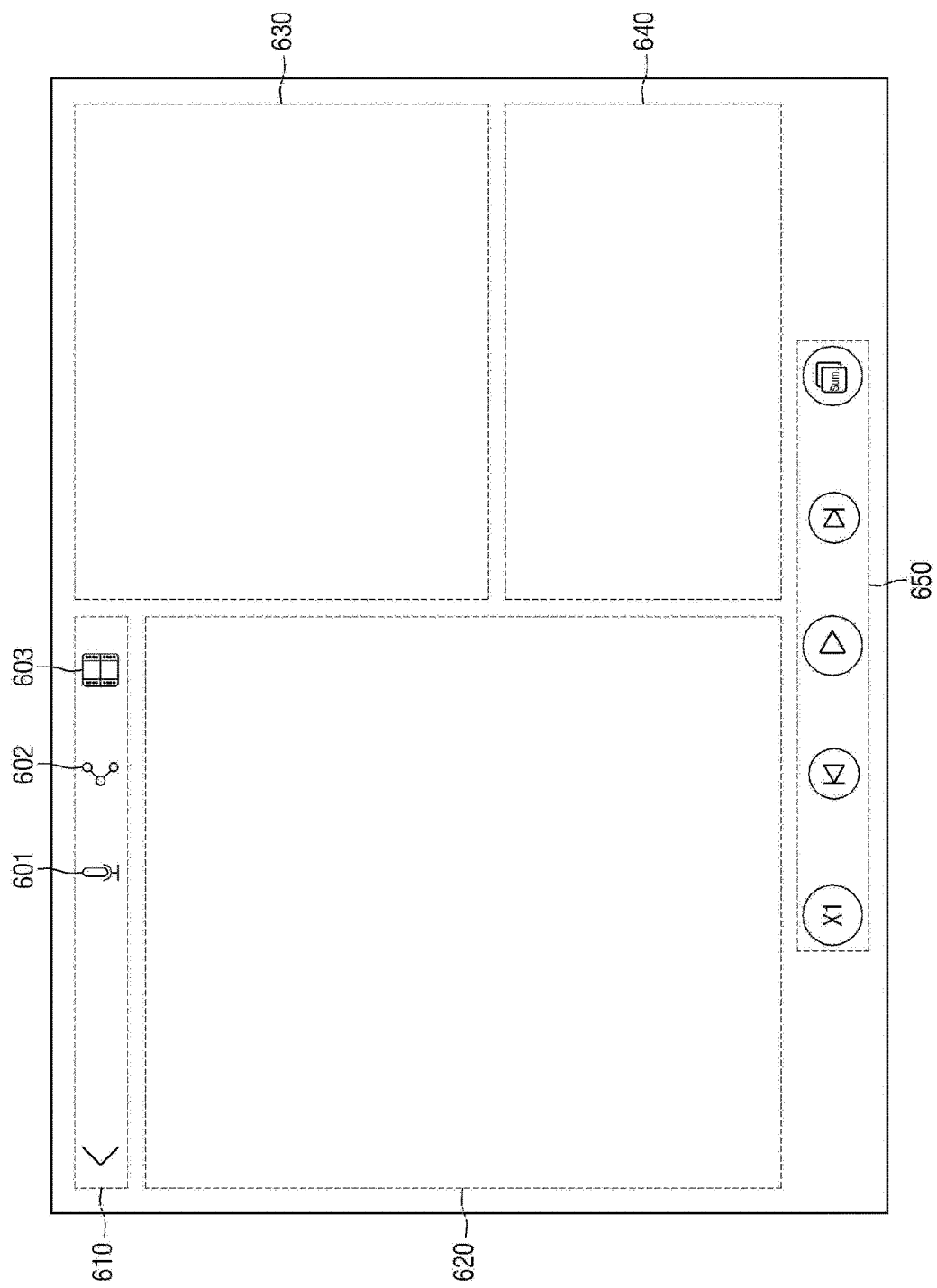
FIG. 21 is another display screen illustrating a generated calculation value and a motion image of a user at the same time.
Figure 22:
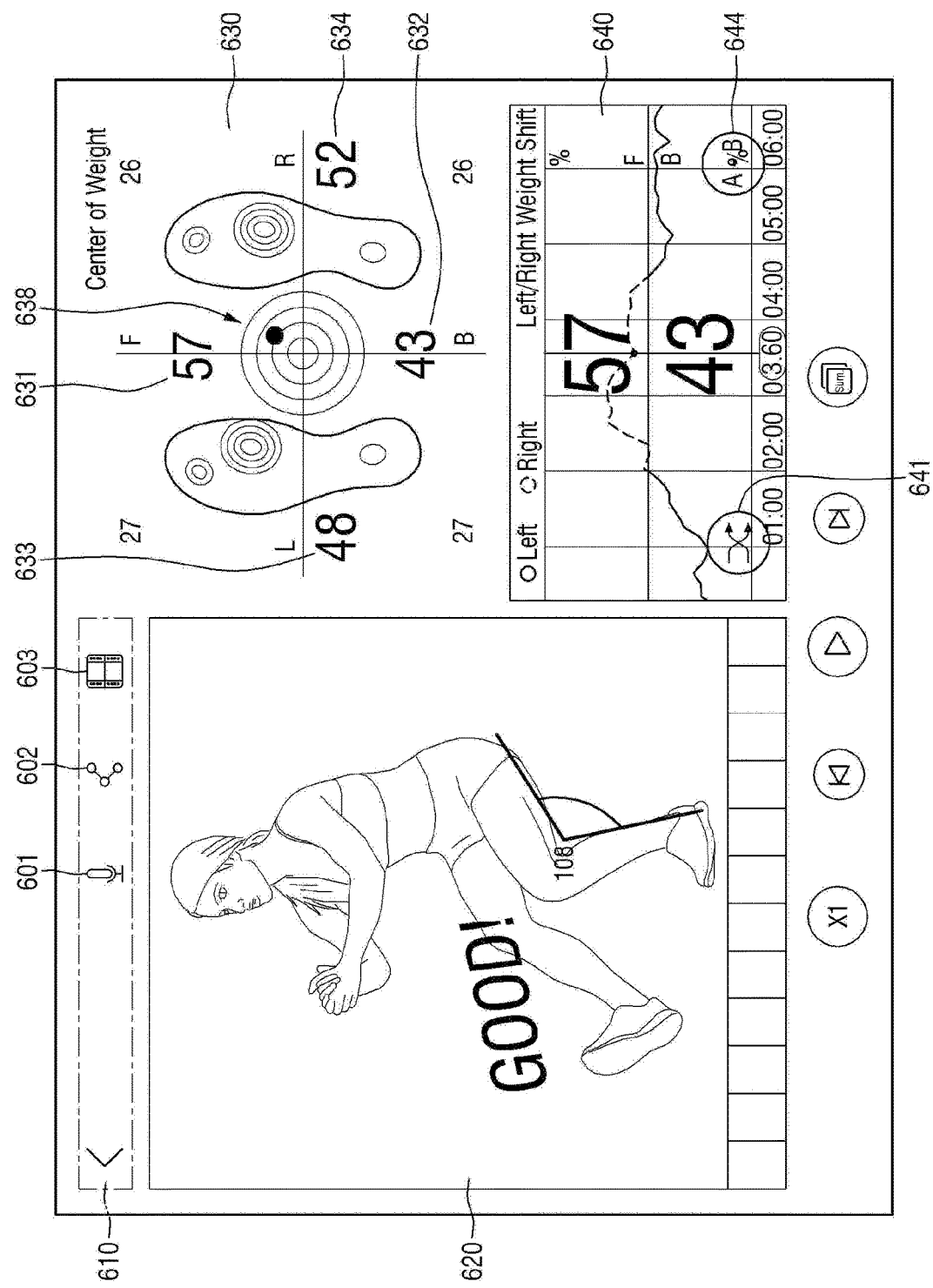
FIG. 22 is an example of a display screen of FIG. 21.

FIG. 21 is another display screen for illustrating a generated calculated value and a motion image of a user at the same time. FIG. 22 is an example of a display screen of FIG. 21.

Referring to FIGS. 21 and 22, after a user wears shoes according to the above-described some embodiments of the present invention, a motion image of the user (walking, running, playing golf, playing baseball, fitness, and the like) is captured. During image-capturing, a plurality of sensing values are sensed by a plurality of sensors in the shoes. At the same as image capturing or after image capturing is finished, at least one calculation value is generated by using the plurality of sensing values.

The motion image of the user may be displayed with at least one sensing value or at least one calculation value.

In detail, for example, the display screen may include a first screen 620, a second screen 630, a third screen 640, a first control area 610, and a second control area 650.

In the first screen 620, the motion image of the user is displayed. The motion image of the user may be a pre-captured image or an image which is being captured.

In the second screen 630 and the third screen 640, the sensing values or the calculation values obtained from the shoes of the user in the motion image are displayed.

For example, in the second screen 630, a left shoe model, a right shoe model, and COW may be displayed at the same time (refer to FIG. 17).

In the third screen 640, a change of a calculation value R_RA_LA2, a calculation value R_FRT_BCK2, or calculation values RA and LA is displayed (refer to FIGS. 18, 19, and 20). According to a selection of the user, one of the calculation value R_RA_LA2, the calculation value R_FRT_BCK2, and the calculation values RA and LA may be shown. For example, when a conversion key 641 in the third screen 640 of FIG. 22 is pushed, for example, the third screen 649 may be converted from the screen of FIG. 18 into the screen of FIG. 19. When the conversion key 641 is pushed again, the third screen 640 may be converted from the screen of FIG. 19 into the screen of FIG. 20.

Otherwise, at least one of the above-described variety of calculations values RF, RB, RA, LF, LB, LA, FRT, BCK, R_RF_LF1, R_RF_LF2, R_RB_LB1, R_RB_LB2, R_RA_LA1, R_RA_LA2, R_FRT_BCK1, and R_FRT_BCK2 may be displayed.

Meanwhile, when a section repeating key 644 of FIG. 22 is pushed, images of a motion and calculation values which are displayed in the first screen 620 to the third screen 640 are repeated section by section.

Meanwhile, the first control area 610 may include a video-recording key/sound-recording key 601, a share key 602, and a comparison key 603.

The user may share captured images, sensing values, calculation values, and the like with other people (for example, an instructor, a trainer, and the like) by pushing the share key 602.

Sequentially, the instructor (or the trainer and the like) may correct a posture and the like of the user simultaneously while watching the captured image, the sensing values, and the calculation values. In detail, the instructor may push the video-recording key/sound-recording key 601 and then may verbally explain well-executed points, poorly-executed points, points for correction, and the like while also writing by hand on the display module. In FIG. 22, for example, it is shown that the instructor handwrites evaluation (GOOD!), an angle (108°), and the like. The explanation may be recorded as video/sound files. The instructor may give the user feedback by pushing the share key 602.

Also, when the user pushes the comparison key 603, the captured images, the sensing values, and the calculation values may be compared with captured images, sensing values, and calculation values of another user. Here, the other user may be an acquaintance, such as a user's friend and the like. Otherwise, the other user may be a professional player or the instructor (trainer). The captured images, the sensing values, the calculation values, and the like of the other user are prestored in a server or a storage device. When the user pushes the comparison key 603, the captured images, the sensing values, the calculation values, and the like of the other user may be provided from the server or the storage device. An exemplary image after the comparison key 603 is pushed is like FIG. 23.

Figure 23:
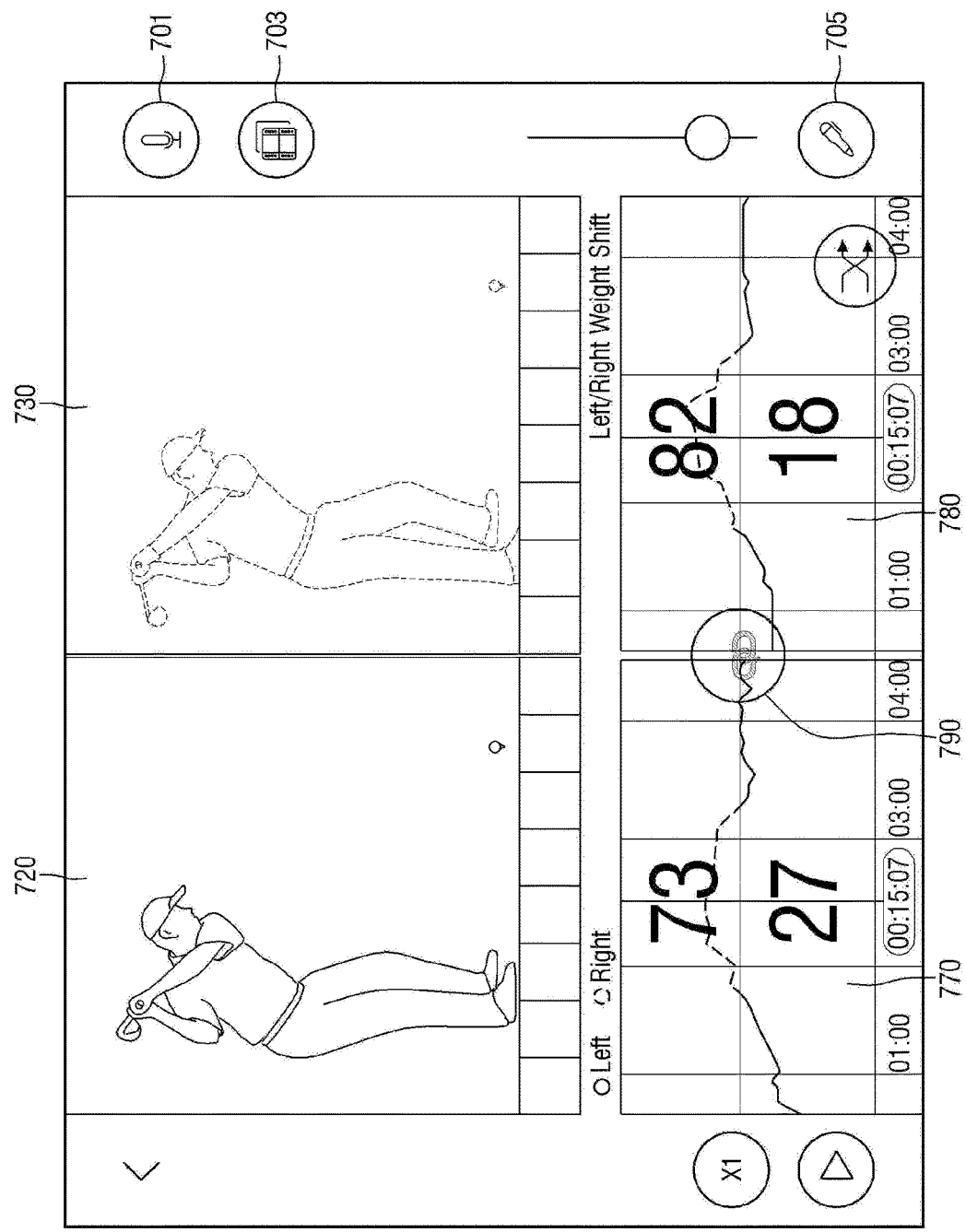
FIG. 23 is a display screen illustrating compared images of the user and another user.

FIG. 23 is a display screen for illustrating compared images of the user and another user.

Referring to FIG. 23, a fourth screen 720 and a fifth screen 730 are displayed at the same time. For example, an image of the user may be displayed in the fourth screen 720, and an image of the other user (professional player, instructor (trainer), and the like) may be displayed in the fifth screen 730.

In a sixth screen 770, sensing values or calculation values of the user of the fourth screen 720 may be displayed.

In a seventh screen 780, sensing values or calculation values of the user of the fifth screen 730 may be displayed.

A reference numeral 701 is a video-recording key/sound-recording key. A reference numeral 705 may be a handwriting key. When the user or another user (instructor, trainer, and the like) pushes the handwriting key 705, evaluation, explanation, and the like may be written on the screen of the display module.

Here, a reference numeral 790 is a combination key. When the user pushes the combination key 790, the fourth screen 720 is combined with the fifth screen 730 and the sixth screen 770 is combined with the seventh screen 780. In detail, before the combination key 790 is pushed, the fourth screen 720 and the fifth screen 730 operate separately. That is, even when an image displayed on the fourth screen 720 is moved back by a time t1, an image displayed on the fifth screen 730 is not moved back. However, after the combination key 790 is pushed, when the user moves back the image displayed on the fourth screen 720 by the time t1, the image displayed on the fifth screen 730 is also moved back by the time t1.

When the combination key 790 is used as described above, a captured image of the user which is displayed on the fourth screen 720 and a captured image of a comparison target which is displayed on the fifth screen 730 may be easily repeated. Accordingly, it is possible to easily compare/contrast the user with the comparison target.

Meanwhile, a reference numeral 703 is an overlap key. When the user pushes the overlap key 730, a display screen shown in FIG. 24 or 25 may be shown.

Figure 24:
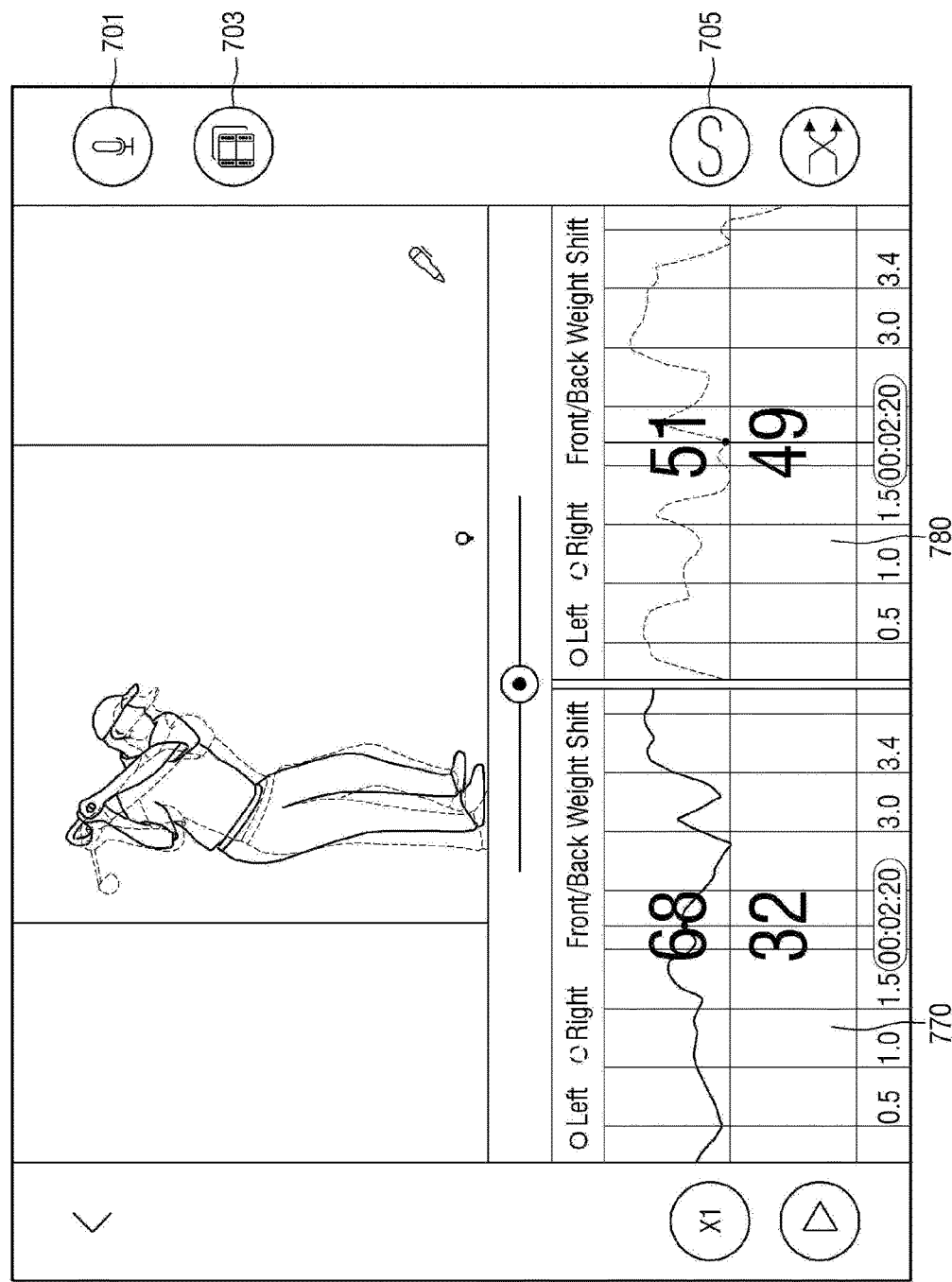
FIGS. 24 and 25 are views illustrating display screens to which an overlap function is applied.
Figure 25:
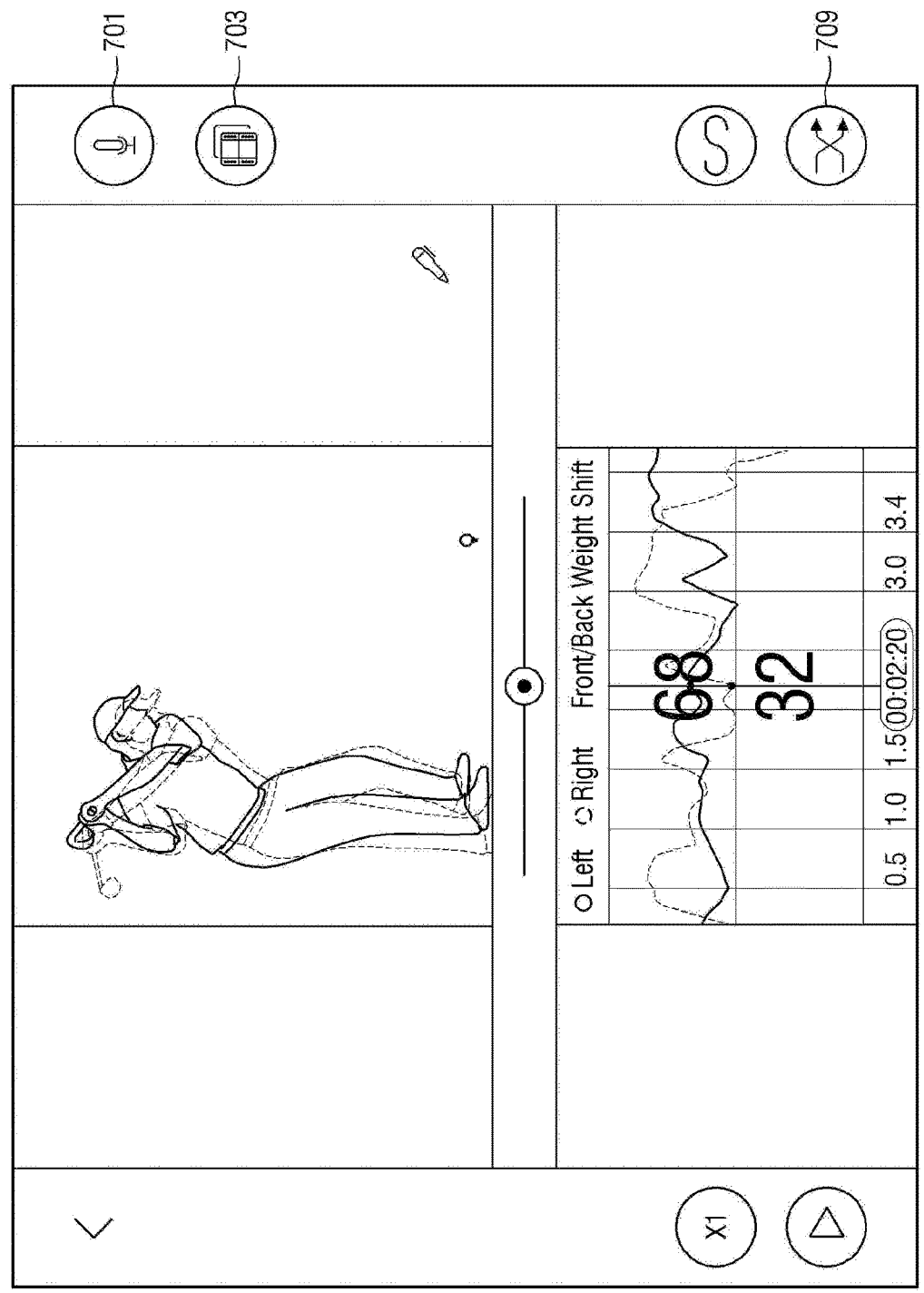

FIGS. 24 and 25 are views illustrating display screens to which an overlap function is applied.

Referring to FIG. 24, the user image of the fourth screen 720 and the image of the other user of fifth screen 730 are overlapped. As described above, an image formed by overlapping the fourth screen 720 with the fifth screen 730 is provided such that it is possible to easily and accurately see a difference in posture between the user and the other user.

Referring to FIG. 25, the overlap images of not only the fourth screen 720 and the fifth screen 730 but also the sixth screen 770 and the seventh screen 780 may be provided. As described above, an image formed by overlapping the sixth screen 770 with the seventh screen 780 is provided such that it is possible to easily and accurately see "a difference in movement of the center of gravity according to a time" between the user and the other user.

Also, on the basis of the difference in posture and a difference in calculation values between the user and the other user in FIGS. 24 and 25, a posture correction of the user may be provided. In detail, through the analysis, the external device 900 or a server connected to the external device 900 may precisely point out the differences between the user and the other user through separate calculations and may provide a solution for overcoming the differences.

Meanwhile, when the user pushes a screen return key 709, the display screen may return to that shown in FIG. 22 or 23.

Although the embodiments of the present invention have been described with reference to the attached drawings, it should be understood by one of ordinary skill in the art that the present invention may be implemented in other detailed forms without changing the technical concept or essential features thereof. Therefore, the above-described embodiments should be understood to be exemplary and not limiting in every aspect.

| Description of Reference Numerals | |
|---|---|
| 100: shoe | 110: outsole |
| 120: upper structure | 105: sensing system |
| 200: flexible circuit board | 201, 202, 203, 204: sensing areas |
| 201a, 202, 203a, 204a: sensors | 211, 212, 213, 214: wires |
| 220: connection area | |
| 400: control module | |
| F: forefoot area | M: mid-foot area |
| R: rear foot area | AR: arch area |
| 610: first control area | 620: first screen |
| 630: second screen | 640: third screen |
| 650: second control area | |

What is claimed is:

1. A shoe comprising:
an outsole which comprises a forefoot area, a mid-foot area, and a rear foot area;
an upper structure combined with the outsole; and
a sensing system embedded in the outsole,
wherein the sensing system comprises a first sensor corresponding to the forefoot area or the mid-foot area and a second sensor corresponding to the rear foot area, and the second sensor is embedded deeper from a top surface of the outsole than the first sensor,
wherein the sensing system comprises a control module comprising a top surface and a rear surface,
wherein the sensing system comprises a first flexible circuit board connected to the top surface of the control module and a second flexible circuit board connected to the rear surface of the control module,
wherein the first sensor is disposed on the first flexible circuit board, and
wherein the second sensor is disposed on the second flexible circuit board.

2. The shoe of claim 1, further comprising a third sensor which is spaced further apart from a front end of the outsole than the first sensor and is disposed closer to the front end of the outsole than the second sensor,
wherein the third sensor is embedded shallower with respect to the top surface of the outsole than the second sensor.

3. The shoe of claim 2, wherein the third sensor is embedded deeper with respect to the top surface of the outsole than the first sensor.

4. The shoe according to claim 2, wherein the first sensor to the third sensor are embedded at depths from 10% to 70% from the top surface of the outsole.

5. The shoe of claim 4, wherein the first sensor to the third sensor are embedded at depths from 10% to 40% from the top surface of the outsole.

6. The shoe of claim 5, wherein the first sensor is embedded at a depth 10% to 20% from the top surface of the outsole,
wherein the third sensor is embedded at a depth 20% to 30% from the top surface of the outsole, and
wherein the second sensor is embedded at a depth 30% to 40% from the top surface of the outsole.

7. The shoe of claim 1, wherein
the first sensor is configured to have a first sensing value according to weight, having a linear shape in a first weight section and a nonlinear shape in a second weight section,
the second sensor is configured to have a second sensing value according to weight, having a nonlinear shape in the first weight section and a linear shape in the second weight section, and
the second weight section corresponds to weights heavier than weights of the first weight section.

8. The shoe of claim 1, wherein the sensing system further comprises a control module which receives sensing signals from the first sensor and the second sensor and communicates with an external device through an antenna, and
wherein the control module is disposed corresponding to an inside of an arch area, and the antenna is disposed further to the arch area than the control module.

9. The shoe of claim 1, wherein each of the first sensor and the second sensor is a pressure-detection sensor having a shape of a film.

10. A shoe comprising:
an outsole;
an upper structure combined with the outsole; and
a sensing system embedded in the outsole,
wherein the sensing system comprises a first sensor and a second sensor,
wherein the first sensor is disposed closer to a front end of the outsole than the second sensor, and a disposition depth of the first sensor is shallower than a disposition depth of the second sensor,
wherein the sensing system comprises a control module comprising a top surface and a rear surface,
wherein the sensing system comprises a first flexible circuit board connected to the top surface of the control module and a second flexible circuit board connected to the rear surface of the control module,
wherein the first sensor is disposed on the first flexible circuit board, and
wherein the second sensor is disposed on the second flexible circuit board.

11. A shoe comprising:
an outsole which comprises a forefoot area, a mid-foot area, and a rear foot area;
an upper structure combined with the outsole; and
a sensing system embedded in the outsole,
wherein the sensing system comprises a first sensor corresponding to the forefoot area or the mid-foot area and a second sensor corresponding to the rear foot area,
wherein the shoe comprises a first weight section and a second weight section heavier than the first weight section,
wherein a sensing value of the first sensor according to weight has a linear shape in the first weight section and a nonlinear shape in the second weight section,
wherein a sensing value of the second sensor according to weight has a nonlinear shape in the first weight section and a linear shape in the second weight section,
wherein the sensing system comprises a control module comprising a top surface and a rear surface,
wherein the sensing system comprises a first flexible circuit board connected to the top surface of the control module and a second flexible circuit board connected to the rear surface of the control module,
wherein the first sensor is disposed on the first flexible circuit board, and
wherein the second sensor is disposed on the second flexible circuit board.

* * * * *